United States Patent [19]
Ikezaki

[11] Patent Number: 5,789,250
[45] Date of Patent: Aug. 4, 1998

[54] TASTE MEASURING METHOD USING TASTE SENSOR WITH MOLECULAR FILM

[75] Inventor: Hidekazu Ikezaki, Isehara, Japan

[73] Assignees: Anritsu Corporation, Tokyo; Kiyoshi Toko, Fukuoka-ken, both of Japan

[21] Appl. No.: 737,838

[22] PCT Filed: Mar. 29, 1996

[86] PCT No.: PCT/JP96/00844

§ 371 Date: Nov. 21, 1996

§ 102(e) Date: Nov. 21, 1996

[87] PCT Pub. No.: WO96/30753

PCT Pub. Date: Oct. 3, 1996

[30] Foreign Application Priority Data

Mar. 30, 1995 [JP] Japan .................. 7-097863

[51] Int. Cl.[6] .................................................. G01N 27/06
[52] U.S. Cl. ............................. 436/20; 436/24; 436/150
[58] Field of Search ..................... 436/20, 24, 149–150, 436/163

[56] References Cited

U.S. PATENT DOCUMENTS

| 5,302,262 | 4/1994 | Yamafuji et al. | 204/153.12 |
| 5,482,855 | 1/1996 | Yamafuji et al. | 435/287.1 |

FOREIGN PATENT DOCUMENTS

| 0 410 356 A1 | 1/1991 | European Pat. Off. . |
| 0 464 820 A1 | 1/1992 | European Pat. Off. . |
| 62-187252 | 8/1987 | Japan . |
| 3-54446 | 3/1991 | Japan . |
| 4-64053 | 2/1992 | Japan . |
| 4-238263 | 8/1992 | Japan . |
| 4-297863 | 10/1992 | Japan . |
| 5-99896 | 4/1993 | Japan . |
| 6-174688 | 6/1994 | Japan . |

OTHER PUBLICATIONS

Y. Kawamura et al; "Umami: A Basic Taste"; 1987; pp. 75–93; Marcel Dekker, Inc.
"Taste Sensor More Sensitive than Man"; Nikkei Science, Oct. 1991; pp. 67–76 (Contest Result of 20th Anniversary Memorial Articles). Both Japanese & English enclosed.

Primary Examiner—Lyle A. Alexander
Attorney, Agent, or Firm—Frishauf, Holtz, Goodman, Langer & Chick

[57] ABSTRACT

A taste measurement method using a taste sensor with a molecular film for an amphiphatic or bitter substance comprises dipping the taste sensor in the target measurement solution for a predetermined period of time; removing, from the target measurement solution, the taste sensor which has been dipped in the target measurement solution for the predetermined period of time, without obtaining a sensor response; and subsequently dipping the taste sensor in a reference solution to obtain a sensor response, wherein the sensor response is defined as the taste information of the target measurement solution. Another taste measurement method comprises dipping the taste sensor in a first reference solution to obtain a first sensor response; after the first sensor response is obtained, dipping the taste sensor removed from the first reference solution in a target measurement solution for a predetermined period of time; removing, from the target measurement solution, the taste sensor which has been dipped in the target measurement solution for the predetermined period of time, without obtaining a sensor response; subsequently dipping the taste sensor in a second reference solution to obtain a second sensor response; and obtaining the difference between the first and second sensor responses, wherein the difference is defined as the taste information of the target measurement solution.

14 Claims, 26 Drawing Sheets

STABILIZATION SOLUTION AND REFERENCE SOLUTION ARE SEPARATE AND SAMPLE CLEANING SOLUTION IS USED

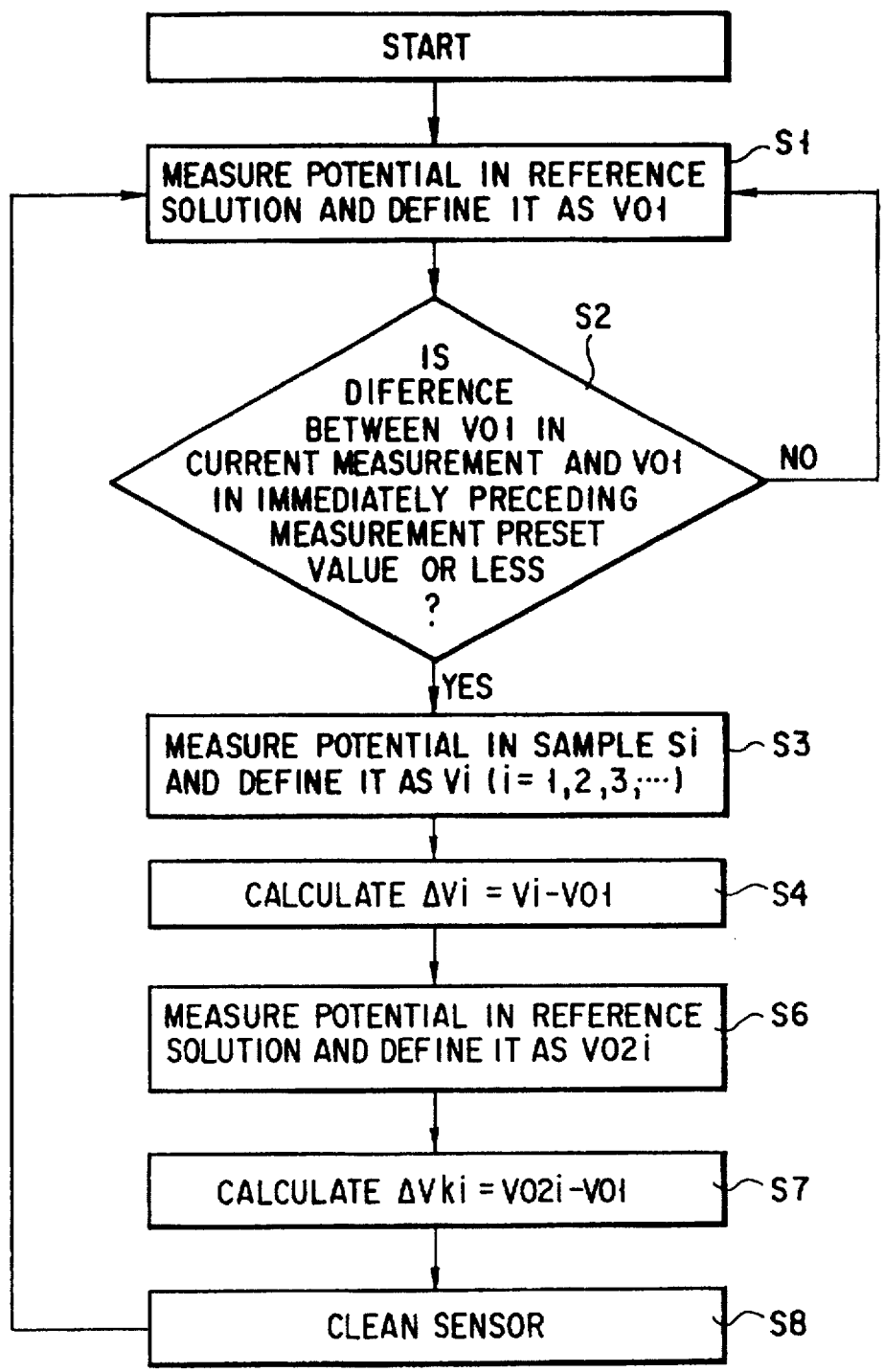
F I G. 1

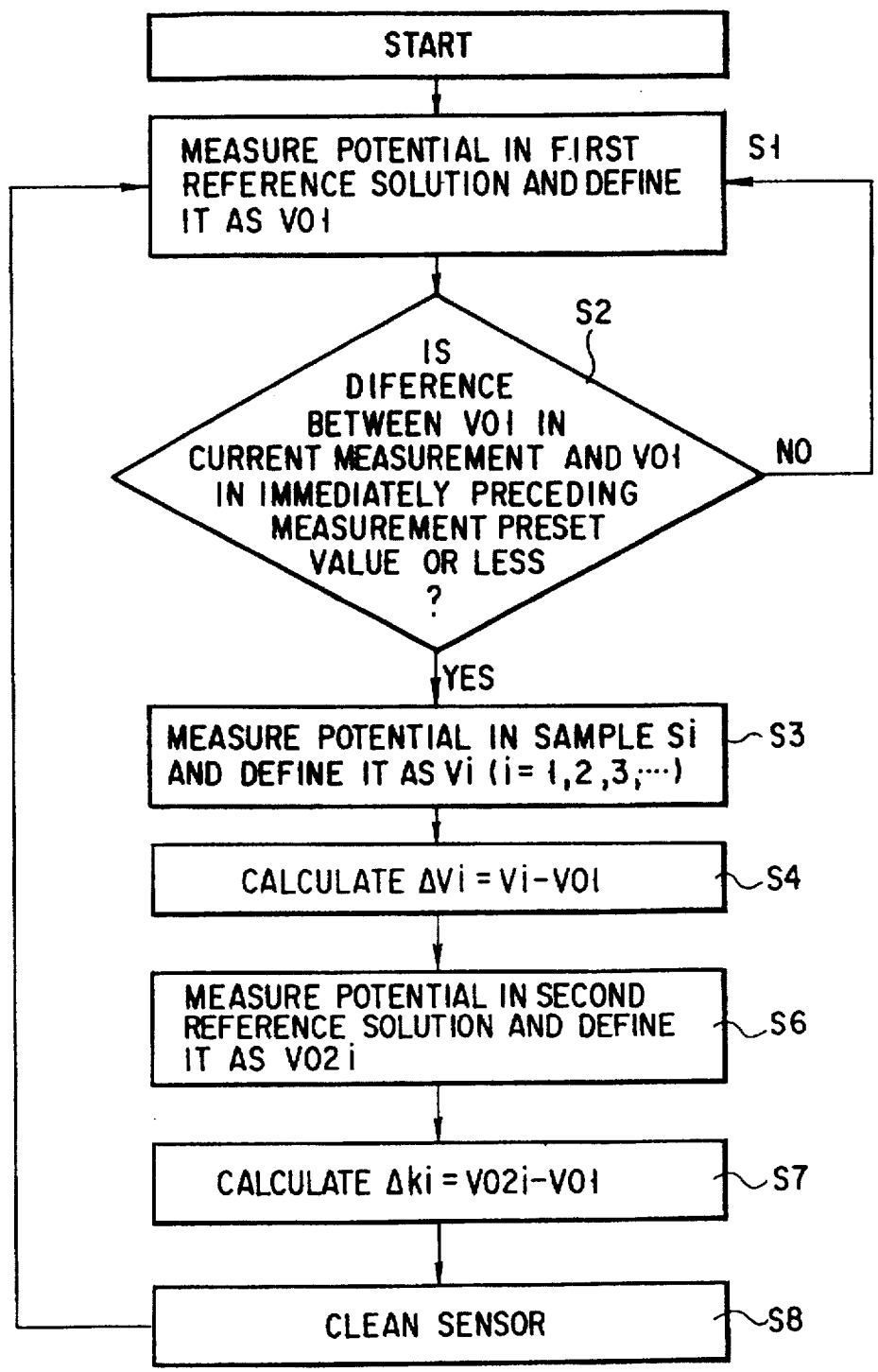
F I G. 2

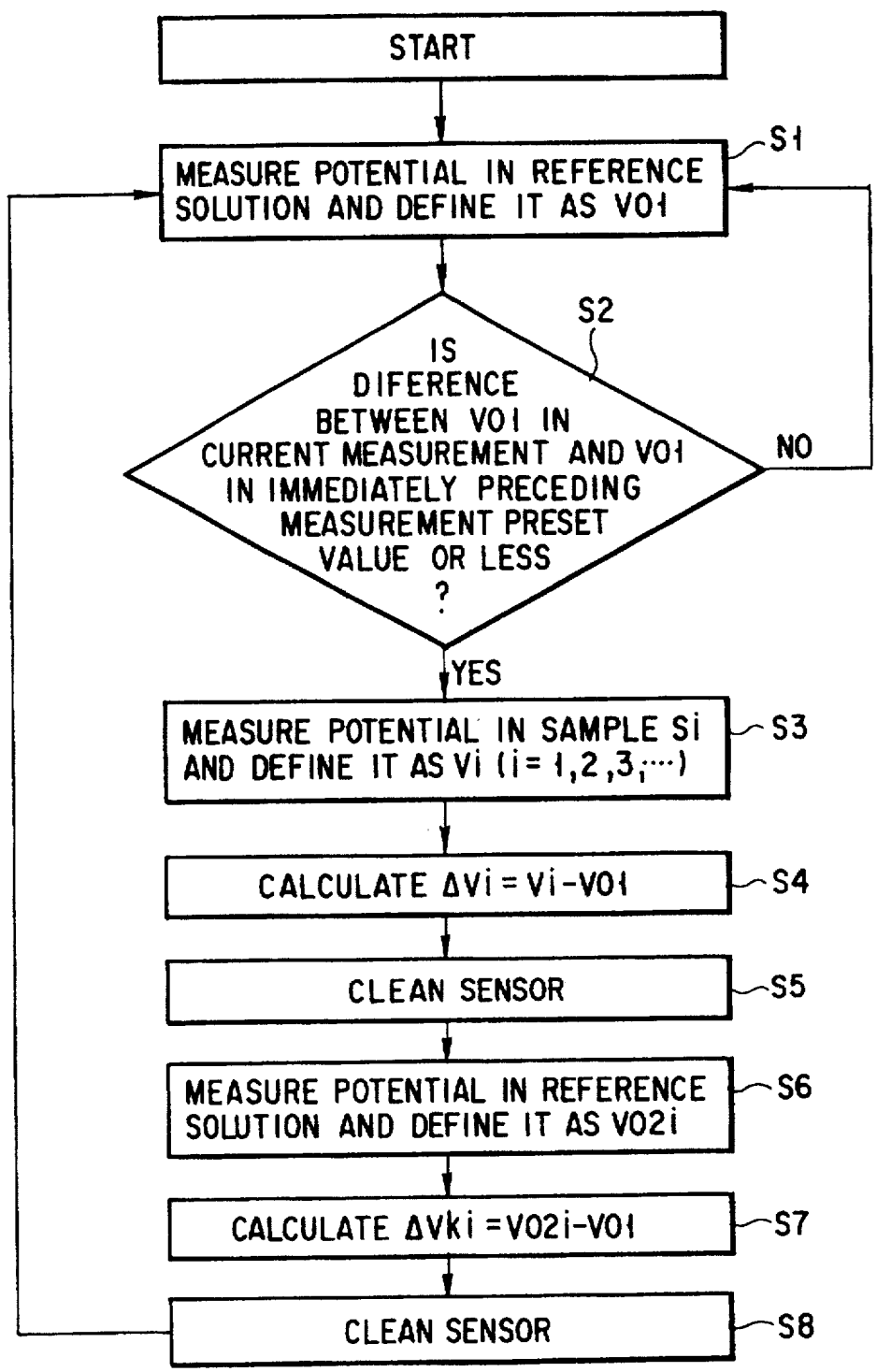
F I G. 3

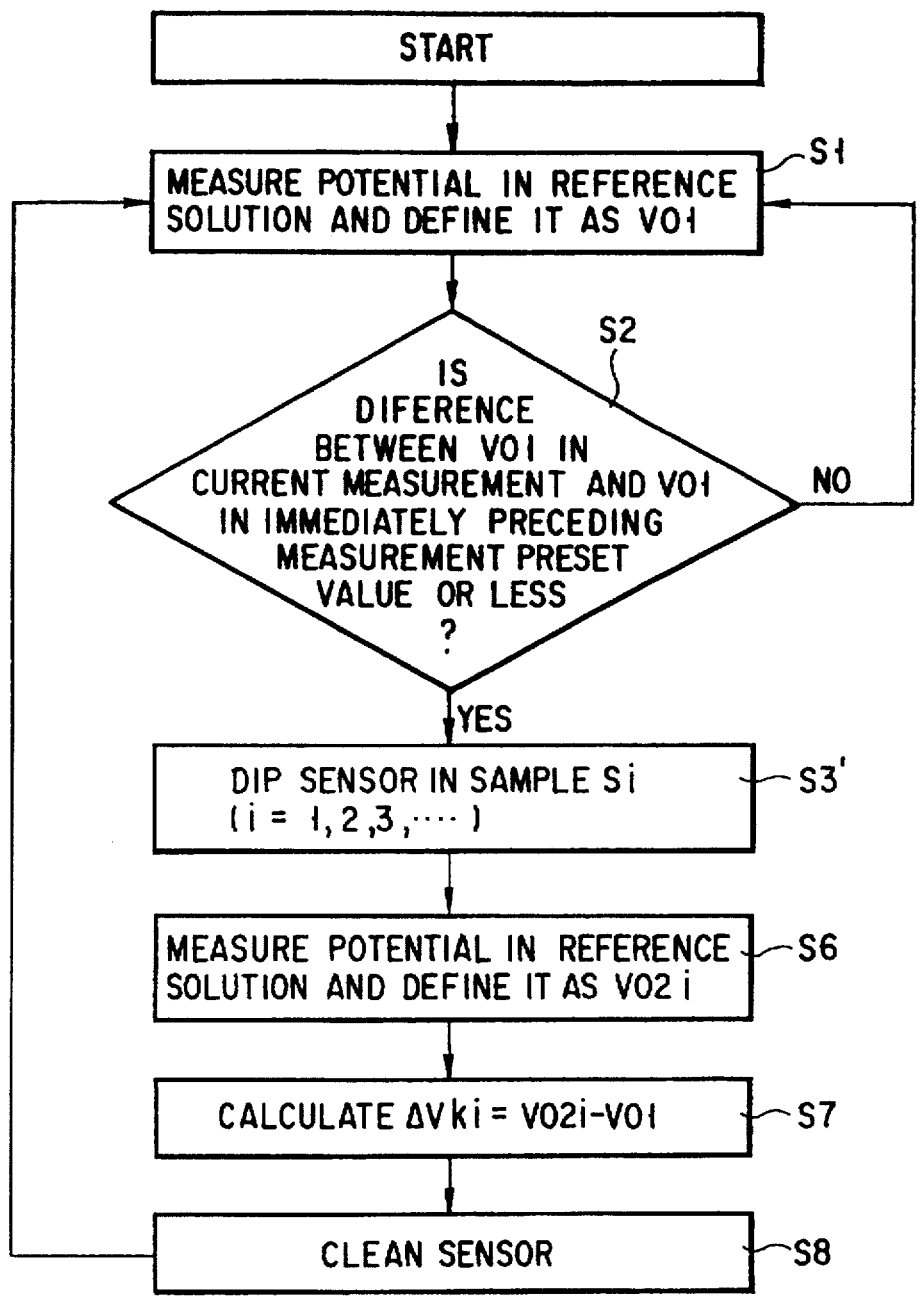
F I G. 4

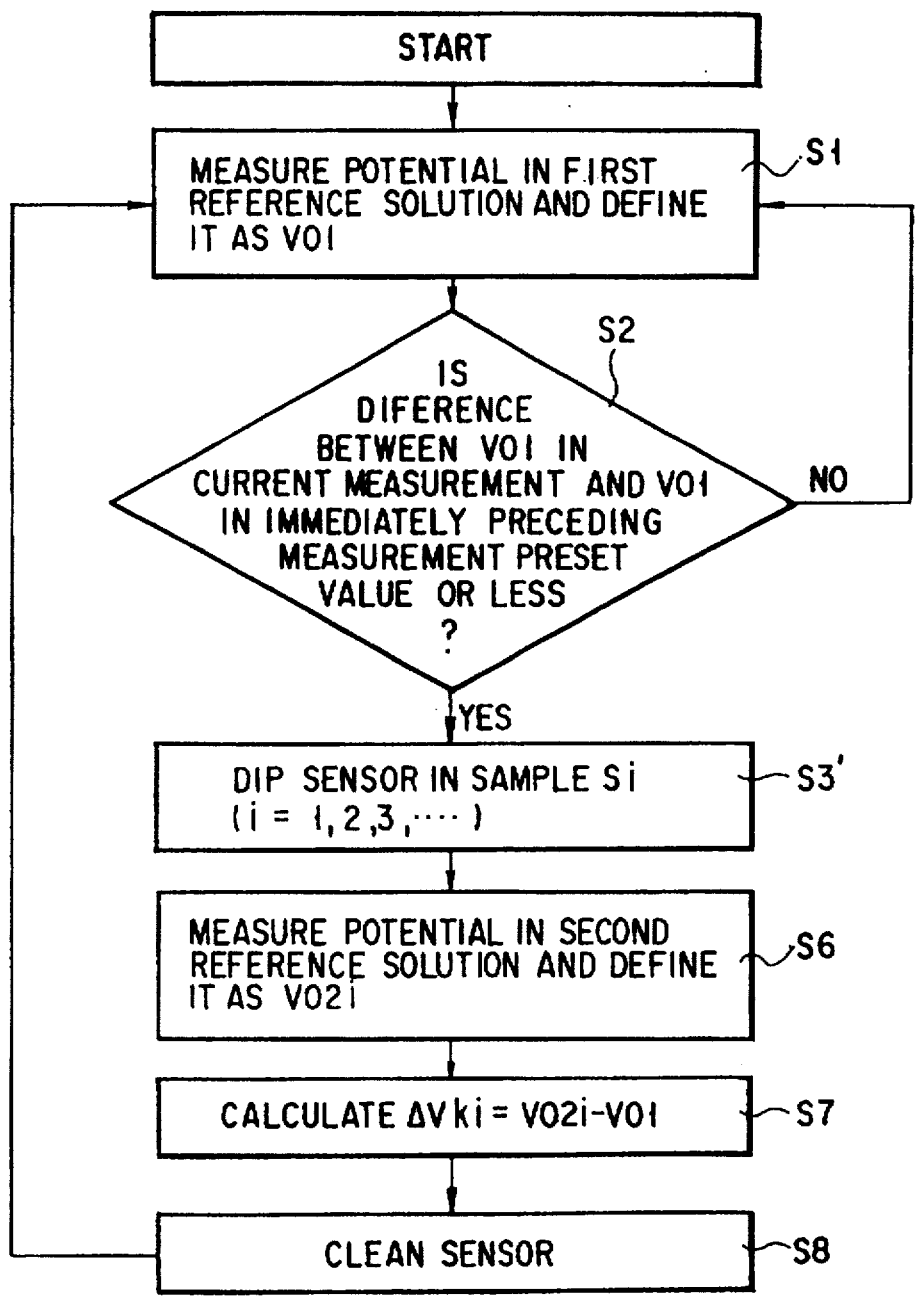
F I G. 5

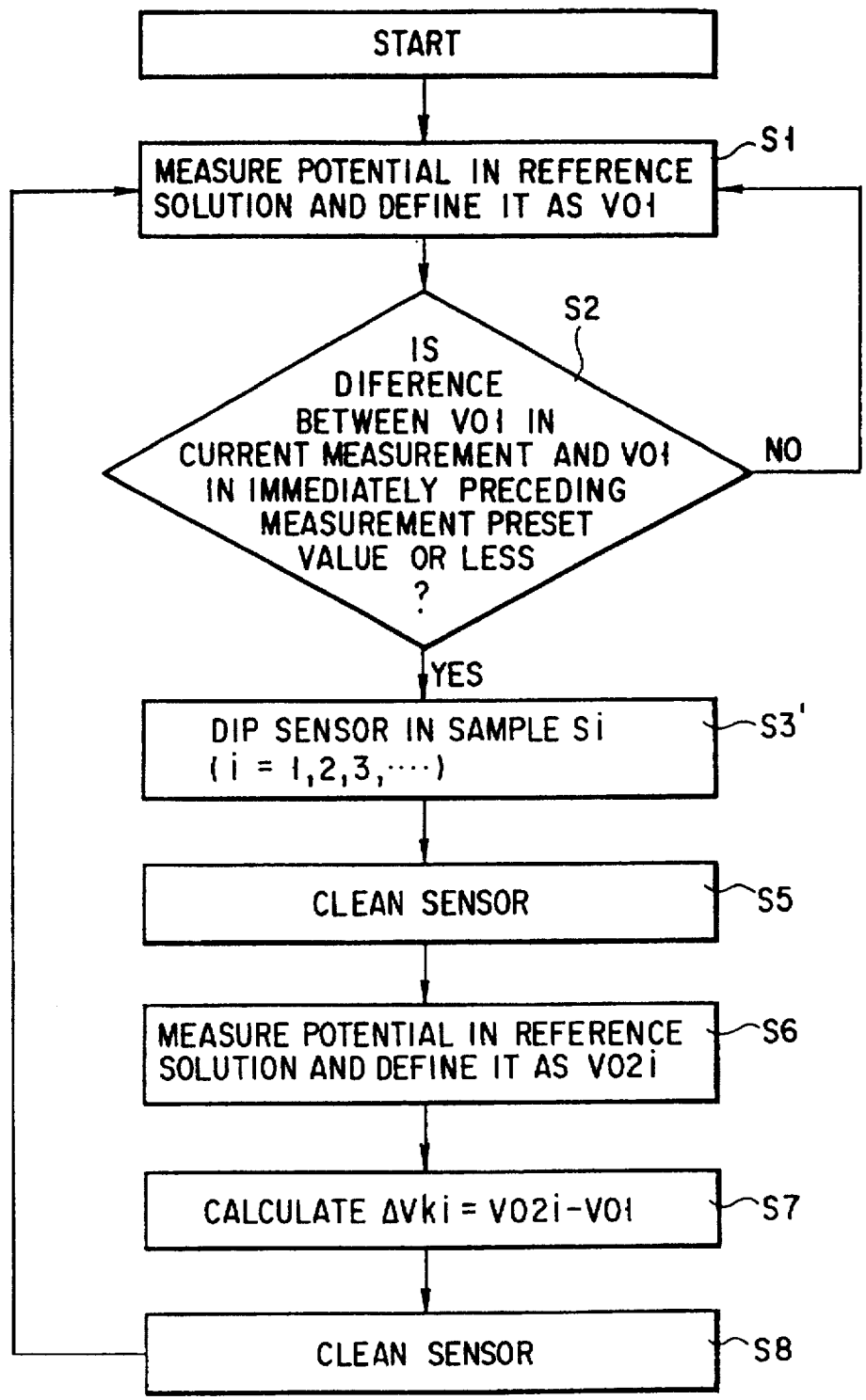
F I G. 6

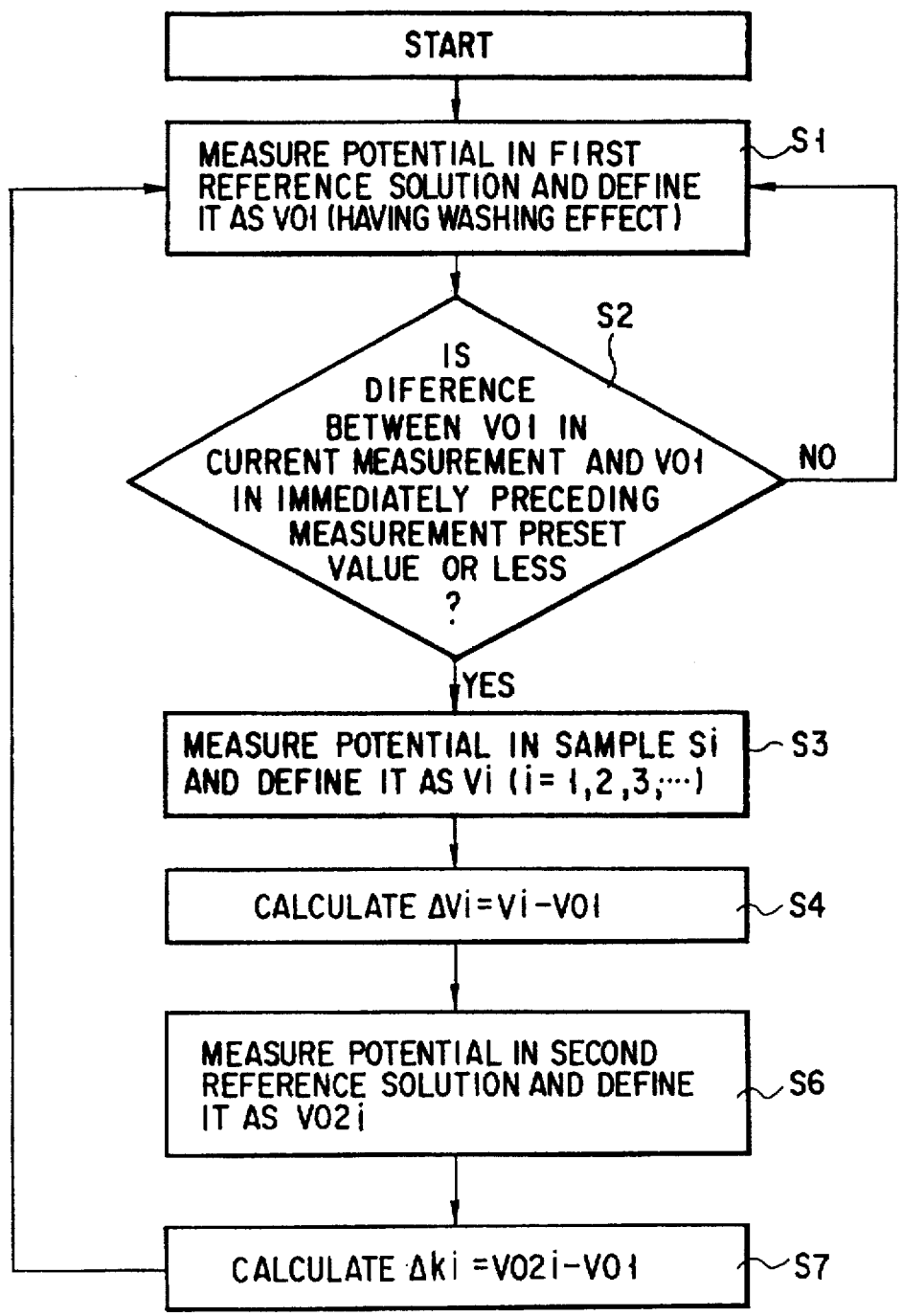
F I G. 7

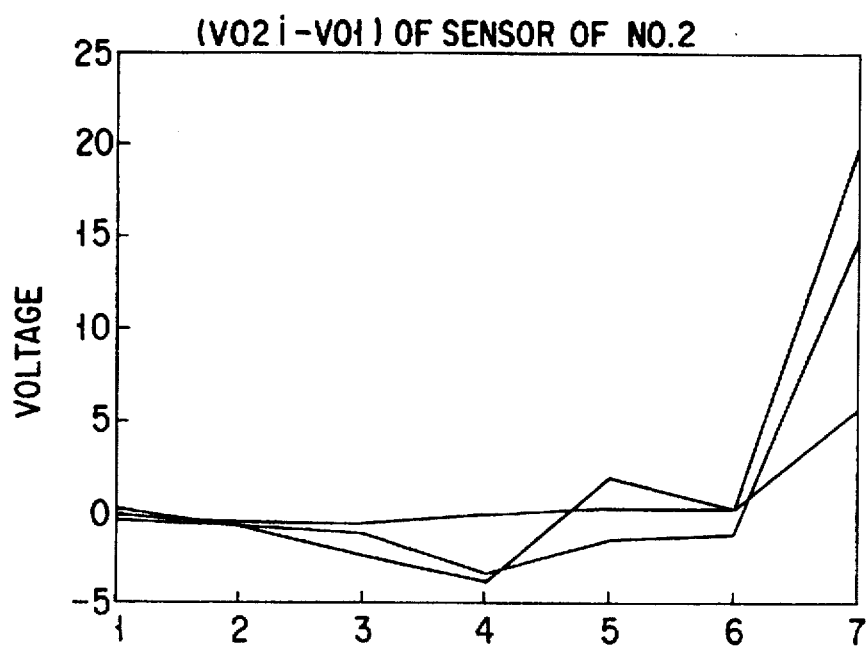
F I G. 9A
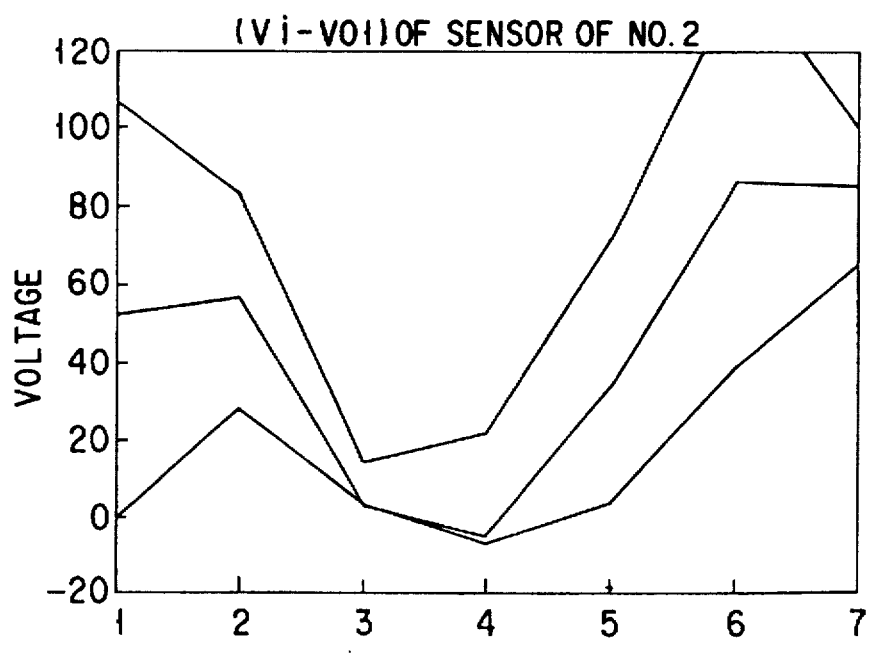
F I G. 9B

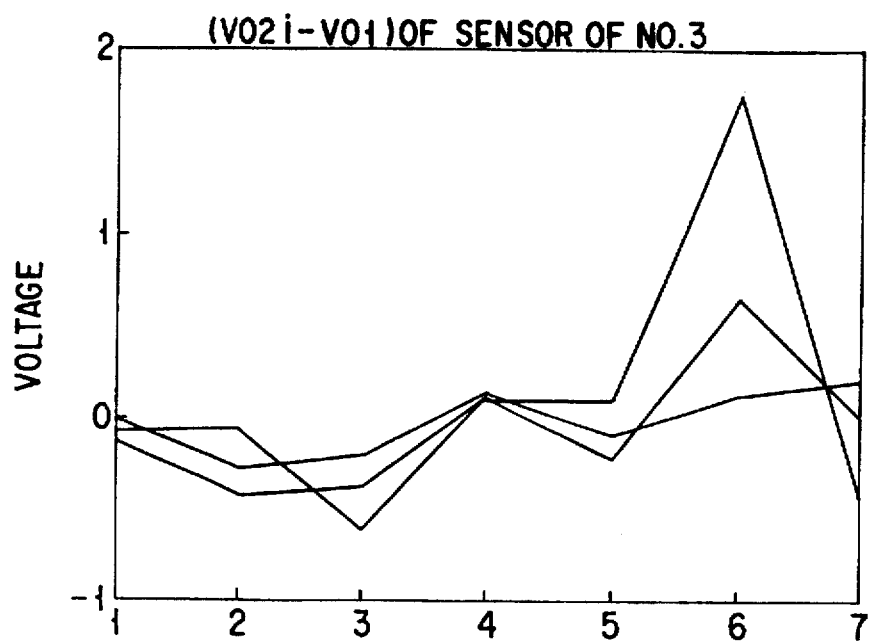
F I G. 10A
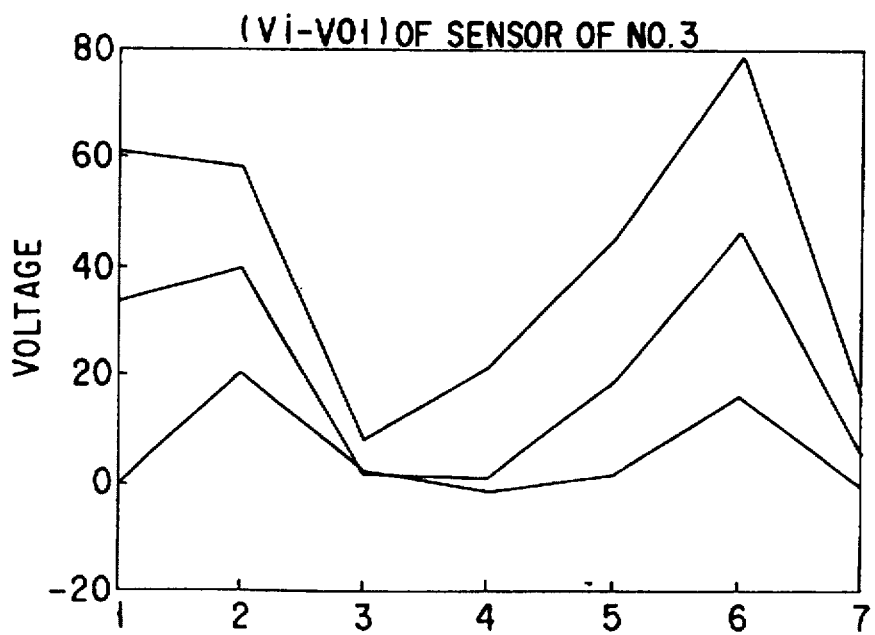
F I G. 10B

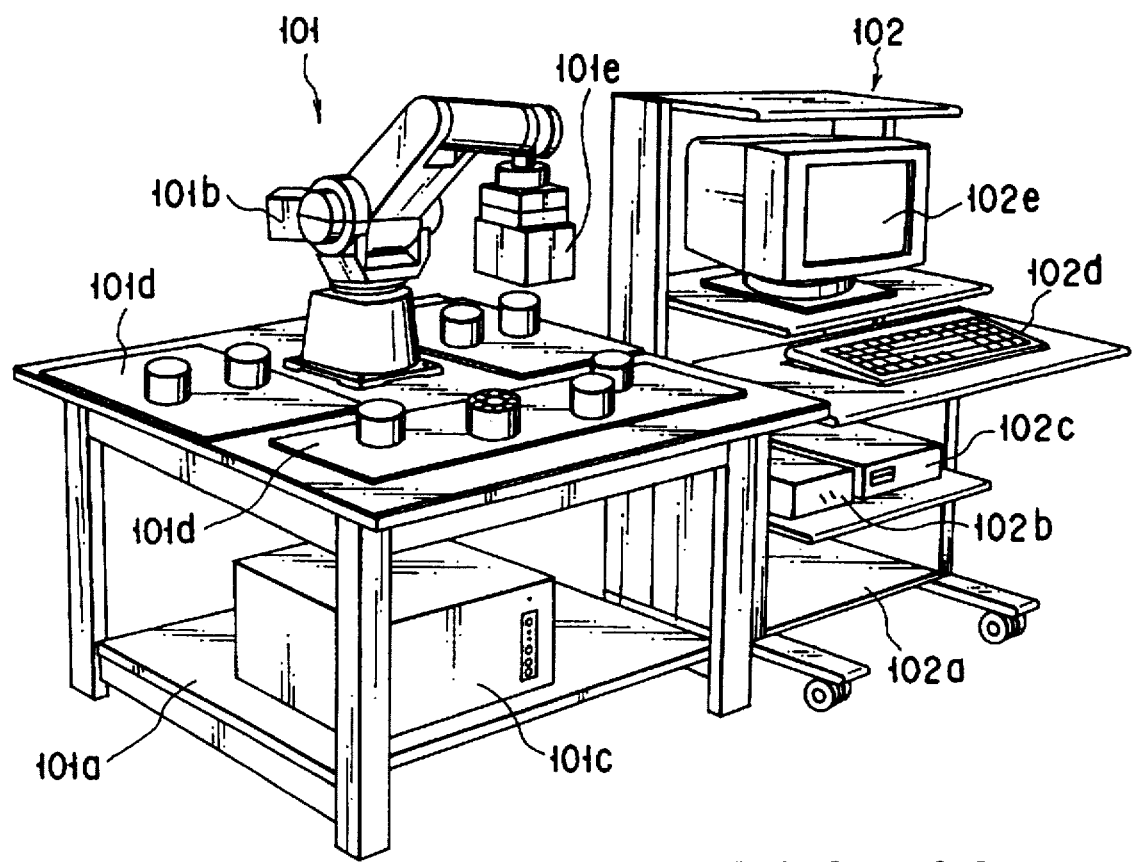
F I G. 20
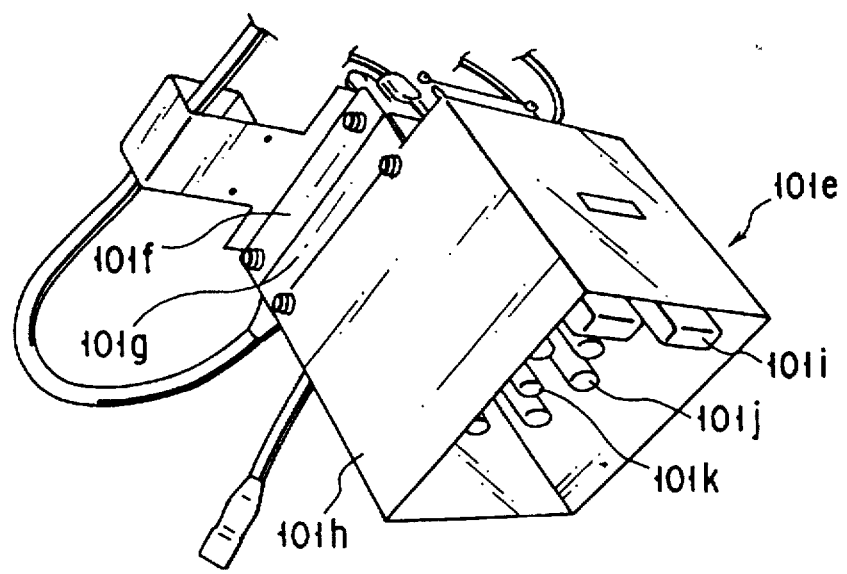
F I G. 21

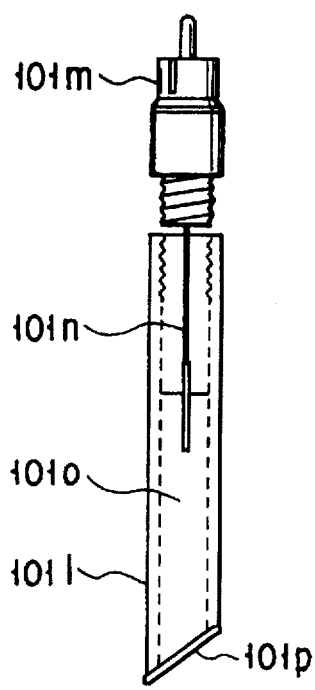
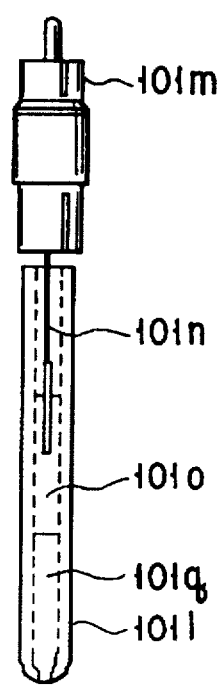
FIG. 22A    FIG. 22B
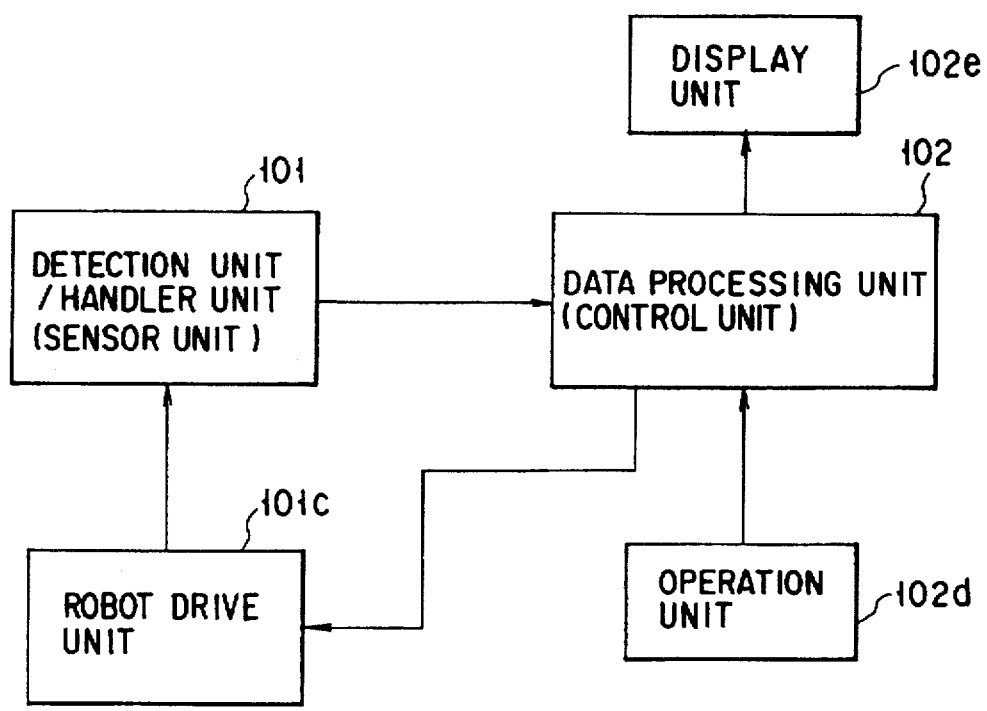
FIG. 23

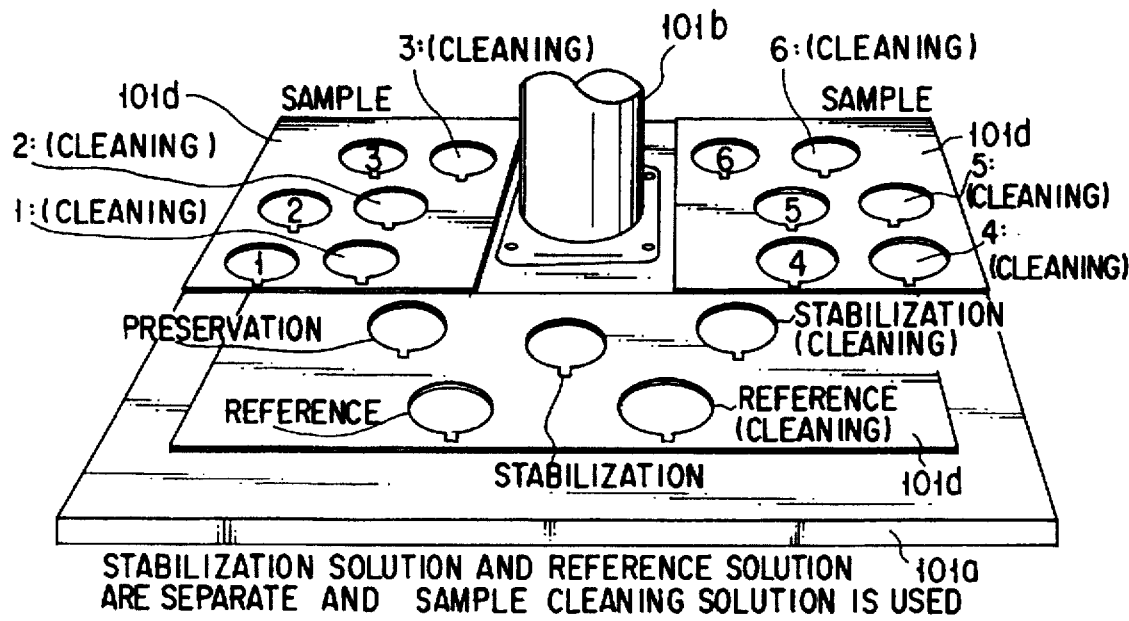
F I G. 24A
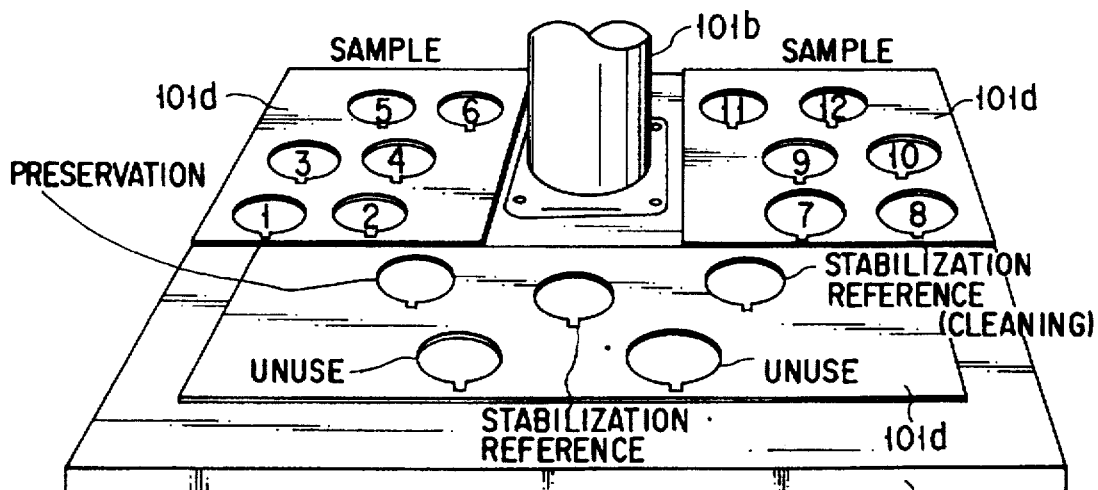
F I G. 24B

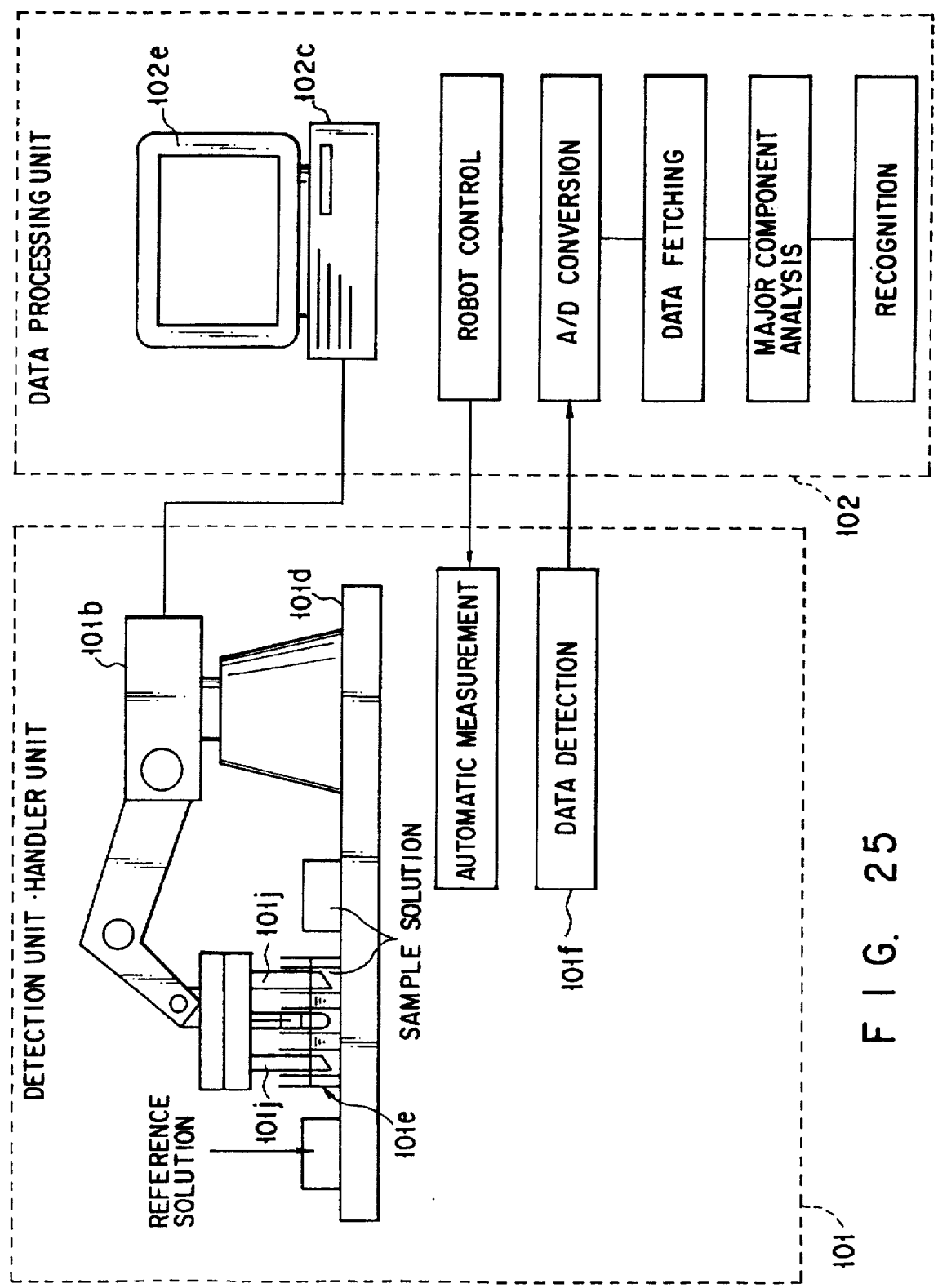
F I G. 25

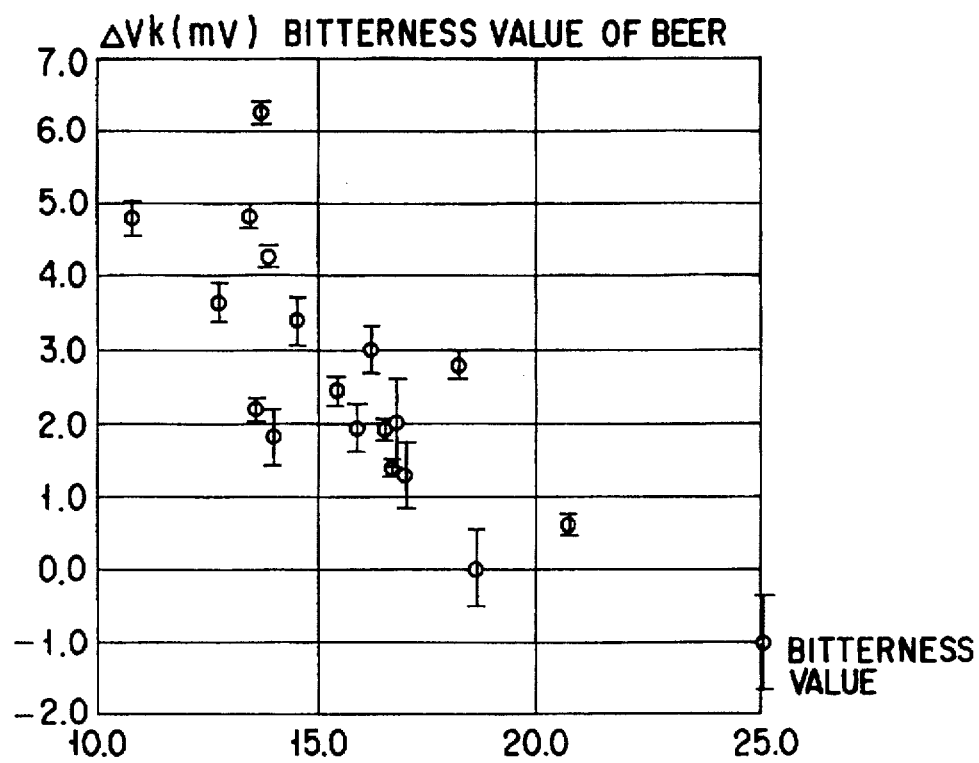
F I G. 27A
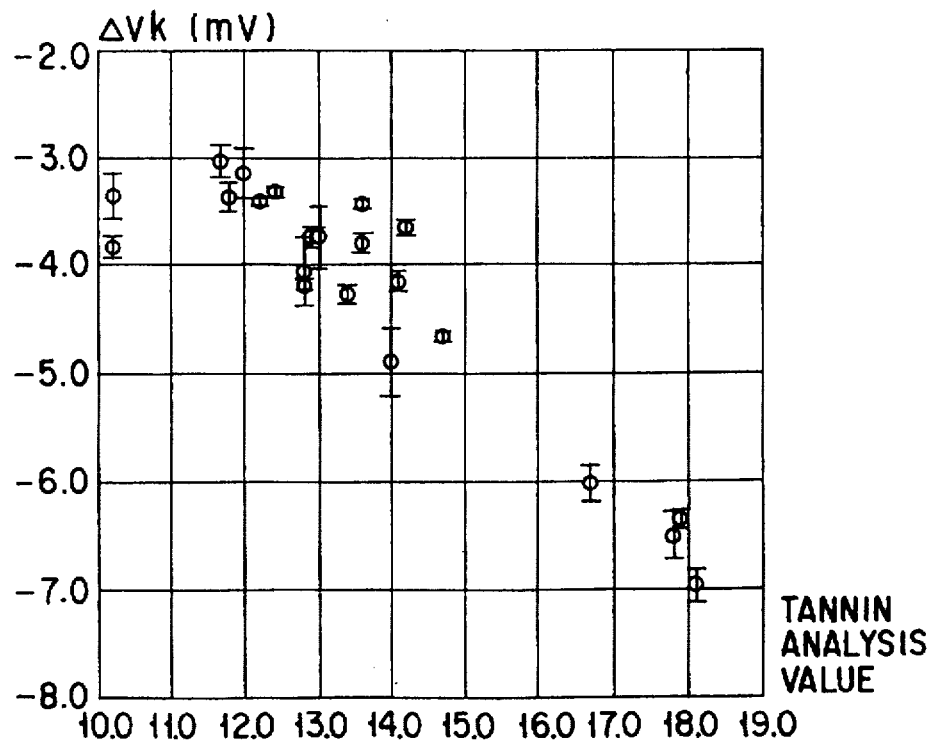
F I G. 27B

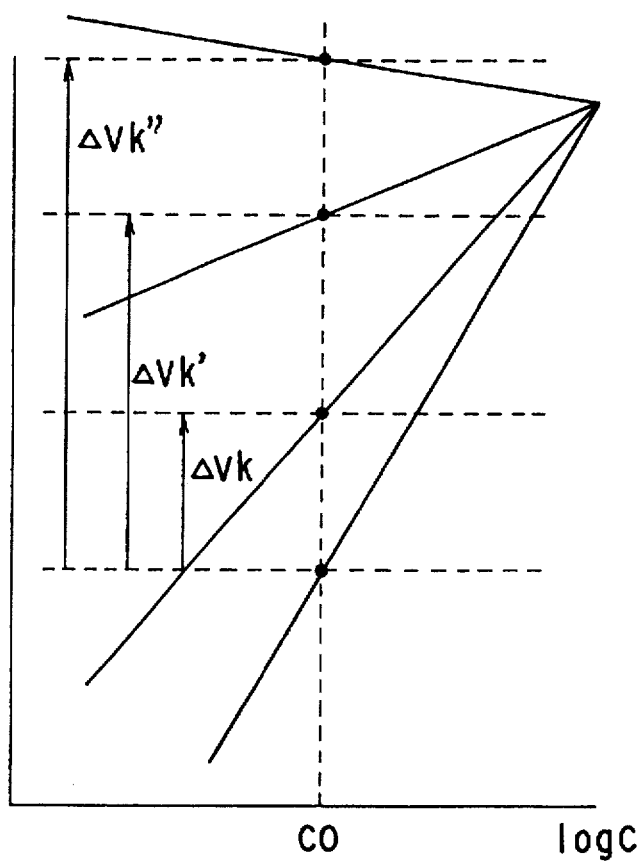
F I G. 28

TASTE MEASURING METHOD USING TASTE SENSOR WITH MOLECULAR FILM

This application is the national filing of PCT/JP96/00844.

TECHNICAL FIELD

The present invention relates to a method of measuring differences in tastes of, e.g., foods and beverages using a taste sensor with a molecular film for an amphiphatic or bitter substance, so that the molecular film can act for the sense of taste as one of the five human senses and, more particularly, to an effective taste measuring method for measuring tastes such as bitterness and umami (many taste substances exhibiting bitterness and umami have adsorption properties to the above molecular film).

In this specification, terms of "taste", "co-washing", "cleaning", and "adsorption" are used in the following meanings.

As well known, the basic taste elements are said to include saltiness, sweetness, bitterness, sourness, and umami (see Umami: A Basic Taste, Marcel Dekker, Inc. 1987), and each taste element has differences in degree.

As for "tastes", assume that differences in tastes which can be evaluated by the human sense of taste or differences in degree of saltiness, for example, (the same kind of taste), can be grasped as physically measurable quantities. A measurable taste or a difference in taste (comparative or relative taste) is called a "taste".

Of all operations for washing off substances contained in a target measurement solution and attaching to a taste sensor, an operation up to removal of substances adsorbed on a molecular film (to be referred to as an adsorbed substance hereinafter) is called "cleaning" to prevent contamination by another target measurement solution subjected to the next measurement, to distinguish "co-washing" for washing off substances attaching to the taste sensor to the extent that they can be relatively easily washed off when the taste sensor is dipped in a solution from the cleaning.

Adsorption occurs in different degrees such that a weakly adsorbed substance can be removed, but a strongly adsorbed substance cannot be removed. "Adsorption" can be classified into physical adsorption and chemical adsorption from the academic standpoint. A variety of forces acting between atoms or molecules are available together with various combinations of atoms and molecules, and it is therefore difficult to define "adsorption". The adsorption including the manner of attachment of substances which cannot be removed by "co-washing" is called "adsorption" herein.

BACKGROUND ART

A conventional technique for measuring a taste will be described below.

A conventional technique for measuring a taste is, for example, disclosed in Jpn. Pat. Appln. KOKAI Publication No. 62-187252. According to this technique, the concentration of each fundamental taste (basic taste) element, i.e., a taste-exhibiting substance in a measurement target is calculated from the output values of a plurality of taste sensors. Each concentration value is corrected to a value representing the degree of each fundamental taste which matches the human taste to measure the taste.

Each taste sensor described in the above publication is a chemical or physical sensor for selectively detecting a substance exhibiting each basic taste. More specifically, the taste sensor for saltiness is a salt densitometer, the taste sensor for sourness is a hydrogen ion index meter, and the taste sensor for sweetness is a sugar meter using the refractive index of a measurement target solution.

These sensors are used for selective detection. For example, the salt densitometer which is meant to measure the degree of saltiness can measure the concentration of a salt, but cannot measure the concentrations of substances other than salt exhibiting saltiness. Therefore, correction for matching the measurement results with the human tastes has limitations.

This detection is analogous to color detection in which a sensor for detecting a single color is used to obtain a multi-color result.

The present applicants have previously filed a patent application (Jpn. Pat. Appln. KOKAI Publication No. 3-054446; U.S. Pat. No. 5,482,855, and EP 0410356A1) for "Taste Sensor and Its Manufacturing Method". The specification and drawings of this patent application exhibit that a lipid molecular film becomes a sensor of tastes, i.e., a taste sensor acting for the human taste. The lipid molecular film has a structure in which a lipid substance (the lipid substance is a kind of amphiphatic substance) including molecules having both hydrophobic portions and hydrophilic portions is immobilized in a polymer matrix, and the hydrophilic portions of the lipid molecules are aligned on the surface of the matrix.

The model of the lipid molecular film is illustrated by an expression method used in a chemical design method in FIG. 17.

Of the lipid molecules, spherical portions represented by circles represent hydrophilic groups $\underline{a}$, i.e., hydrophilic portions $\underline{a}$, and the atomic arrangements of hydrocarbon chain structures $\underline{b}$ (e.g., alkyl groups) extend from the hydrophilic portions $\underline{a}$.

In FIG. 17, two chains extend to represent one molecule, thereby constituting molecules as a whole.

The chain portions of hydrocarbons are hydrophobic portions $\underline{b}$.

A lipid molecule group 31 is accommodated in a matrix 33 (a surface structure, i.e., a micro-structure having two-dimensional spread) as the surface of a film member 32 such that some lipid molecules are dissolved inside the matrix (e.g., 31' in FIG. 17).

The lipid molecules are accommodated in such a manner that some of the hydrophilic portions are aligned on the surface.

A multichannel taste sensor using this lipid molecular film is obtained, as shown in FIGS. 18(A) and 18(B).

In FIGS. 18A and 18B, three sensing portions of a multichannel array electrode are illustrated.

In the example shown in FIGS. 18A and 18B, holes each having a diameter of 0.5 mm are formed in an acrylic plate base member, and silver round rods are inserted in the holes to obtain electrodes, respectively.

The lipid molecular film is bonded to the base member in contact with the electrodes through buffer layers.

A taste measurement system using the multichannel taste sensor is shown in FIG. 19.

An aqueous solution containing a taste-exhibiting substance is prepared and poured as a target measurement solution 11 in a container 12 such as a beaker.

A taste sensor array 13 manufactured by arranging a lipid membrane and electrodes on an acrylic plate (base member), as described above, was dipped in the target measurement solution.

Before the use, the electrode potential is stabilized in a 1 mmol/l aqueous potassium chloride solution.

Referring to FIG. 19, reference numerals 14-1, ..., 14-8 denote lipid membranes represented by black dots.

A reference electrode 15 serving as an electrode for generating a reference measurement potential is prepared and dipped in the target measurement solution.

The taste sensor array 13 is spaced apart from the reference electrode 15 by a predetermined distance.

A buffer layer 16 consisting of 100 mmol/l of potassium chloride solidified with agar covers the surface of the reference electrode 15. As a result, the electrode system has a structure of silver 2|silver chloride 4|lipid membrane 3 (14)|target measurement solution 12|buffer layer (potassium chloride: 100 mmol/l) 16|silver chloride 4|silver 2.

Electrical signals from the lipid layers are signals of eight channels in FIG. 19. These signals are supplied to buffer amplifiers 19-1, ..., 19-8 through lead wires 17-1, ..., 17-8, respectively.

The outputs from the buffer amplifiers 19 are selectively output by an analog switch (8 channels) 20 to an analog/digital (A/D) converter 21.

An electrical signal from the reference electrode 15 is also supplied to the A/D converter 21 through a lead wire 18. The difference between the reference signal and the potential from each membrane is converted into a digital signal with the A/D converter 21.

This digital signal is appropriately processed for arithmetic operations required for taste measurement by a microcomputer 22 and displayed on an X-Y recorder 23.

In this example, the 8-channel taste sensor is used, and the membranes for the respective channels include lipid molecular films (Table 1) having different response characteristics in response to tastes in order to obtain a variety of taste information capable of reproducing human tastes.

TABLE 1

| No. | Lipid |
| --- | --- |
| 1 | dioctyl phosphate |
| 2 | cholesterol |
| 3 | trioctylmethyl ammonium chloride |
| 4 | oleic acid |
| 5 | n-octadecyl chloride |
| 6 | diphenyl phosphate |
| 7 | decyl alchol |
| 8 | dioctadecyl dimethyl ammonium bromide |
| 9 | lecithin |
| 10 | trimethyl stearyl ammonium chloride |
| 11 | oleyl amine |

The taste sensor defined in the specification of the above-mentioned patent application (Jpn. Pat. Appln. KOKAI Publication No. 3-054446: U.S. Pat. No. 5,482,855 and EP0410356A1) is a faithful taste sensor having physical and chemical properties similar to a tongue as the human gustatory organ. The sensor produces similar outputs for similar tastes even if taste-exhibiting substances are different. It produces some outputs for different tastes.

The above taste sensor corresponds to a sensor capable of detecting multiple colors instead of a single color in color detection.

The present applicants, etc. filed a patent application entitled "Taste Detection Method" (Jpn. Pat. Appln. KOKAI Publication 4-064053: U.S. Pat. No. 5,302,262 and EP 464820A1) of measuring tastes using the above taste sensor.

Slight differences in tastes such as differences in brands of drinks such as beer and differences between lots can be discriminated by the invention of this taste detection method.

This taste detection method will be briefly described below.

More specifically, according to this taste detection method, a solution similar to a target measurement sample solution is used as a reference solution to detect and measure tastes, with good reproducibility, using a taste sensor with a lipid molecular film.

The taste sensor is sufficiently dipped in the reference solution, and a similar stimulus is applied in every measurement using the taste sensor.

The measurement time is selected after the surface potential of the sensor is stabilized and when the internal potential of the sensor is changing slowly. The difference between the measurement values of the reference solution and the target measurement sample solution is calculated.

In this case, if the measurement target is beer, beer or a solution similar to beer is used as the reference solution. The taste sensor is dipped in this reference solution in advance, thereby familiarizing it.

Since this allows the lipid membrane to adsorb, in advance, absorption substances contained in beer, the influences of adsorption substances can be minimized, when various types of beer are measured.

According to this taste detection method, although the sensitivity to a substance adsorptive to the lipid membrane is lowered, the reproducibility can be greatly improved.

An advanced detection method of the above "Taste Detection Method" was filed by some of the present applicants as "Detection Method of Taste" (Jpn. Pat. Appln. KOKAI Publication No. 6-174688).

According to the detection method of a taste of the first invention of the prior application, in order to detect and measure tastes, with good reproducibility, using a molecular film for an amphiphatic or bitter substance including a lipid membrane (to be referred to as a molecular film hereinafter), solutions similar to a sample solution are prepared as first and second reference solutions. The measurements are performed in the order of first reference solution (V0)→second reference solution (Vk)→first reference solution (V0') →sample solution (Vs). The relative value ((Vs−V0')−(Vk−V0)) of the sample solution measurement values from the reference value is calculated to eliminate variations in relative values of continuous drifts of the taste sensor. The use of the first reference solution can eliminate the influences on the measurement values even if the taste of the first reference solution changes.

When the taste of a target measurement solution containing substances adsorptive to the molecular film is to be measured using a taste sensor using the molecular film for an amphiphatic or bitter substance, the first measurement value obtained in use of the taste sensor whose molecular film did not adsorb adsorption substances are different from the second measurement value obtained in use of the taste sensor whose molecular film adsorbed the absorption substances in the first measurement. Although the differences between the two consecutive measurements are reduced gradually, the differences in measurement values between the second measurement and the third measurement, and between the third measurement and the fourth measurement, are still present.

In this case, removal of the adsorbed substances from the molecular film is the best method. Such a method is not conventionally available. When a target measurement solution containing substances adsorbed on the molecular film is to be conventionally measured with a taste sensor having a molecular film, a solution containing components similar to those of the target measurement solution was prepared as the reference solution. The taste sensor was sufficiently dipped in the reference solution, and a substance contained in the reference solution and to be adsorbed in the molecular film was allowed to be adsorbed in the molecular film in advance.

With the above operation, the conventional taste detection method minimizes the influences of the adsorption substance in measurement (stabilization) and improves reproducibility.

According to the conventional taste measurement method, in order to improve reproducibility (stabilization), the taste sensor is sufficiently dipped in the solution containing the components similar to those of the target measurement solution in a stage prior to actual measurement, and the substance to be adsorbed on the membrane (molecular film) is caused to be adsorbed in advance. The actual measurement is then performed. Therefore, (1) the sensitivity to a highly adsorptive taste-exhibiting substance such as a bitter substance is undesirably degraded.

This is not associated with adsorption of the adsorption substances prior to the measurement. A molecular film used in a taste sensor has different response quantities to basic tastes such as sourness, saltiness, sweetness, bitterness, and umami.

For example, a given molecular film responds not only to sourness but also to bitterness more or less. In this manner, the molecular film responds to a plurality of tastes. The response component of the response quantity of the molecular film which corresponds to each basic taste is unknown.

In addition, since an adsorption substance is adsorbed in the molecular film in advance, the properties of the film surface of the taste sensor become uniform, and responses to the basic tastes become similar to each other. (2) It becomes more difficult to distinguish response components corresponding to the respective basic tastes.

The above problems results in a small taste information quantity.

DISCLOSURE OF INVENTION

It is, therefore, an object of the present invention to improve the technique for measuring a taste and increase the taste information quantity in association with the conventional problems described above, and to provide a taste measurement method therefor.

According to the present invention, there is provided a taste measurement method for obtaining taste information of a target measurement solution using a taste sensor with a molecular film for an amphiphatic or bitter substance, comprising the steps of:

dipping the taste sensor in the target measurement solution for a predetermined period of time;
removing, from the target measurement solution, the taste sensor which has been dipped in the target measurement solution for the predetermined period of time;
subsequently dipping the taste sensor in a reference solution to obtain a sensor response, wherein the sensor response is defined as the taste information of the target measurement solution.

According to the present invention, there is also provided a taste measurement method for obtaining taste information of a target measurement solution using a taste sensor with a molecular film for an amphiphatic or bitter substance, comprising the steps of:

dipping the taste sensor in a first reference solution to obtain a first sensor response;
after the first sensor response is obtained, dipping the taste sensor removed from the first reference solution in the target measurement solution for a predetermined period of time;
removing, from the target measurement solution, the taste sensor which has been dipped in the target measurement solution for the predetermined period of time;
subsequently dipping the taste sensor in a second reference solution to obtain a second sensor response; and
obtaining a difference between the first and second sensor responses,
wherein the difference is defined as the taste information of the target measurement solution.

According to the present invention, there is also provided a taste measurement method including the step of cleaning the taste sensor to a desired degree after the step of removing the taste sensor from the target measurement solution.

According to the present invention, there is also provided a taste measurement method including the step of cleaning a desired adsorption substance on the taste sensor after the step of removing the taste sensor from the target measurement solution.

According to the present invention, there is also provided a taste measurement method including the steps of cleaning the taste sensor and measuring a next target measurement solution after the step of obtaining the difference between the first and second sensor responses.

According to the present invention, there is also provided a taste measurement method characterized in that the second reference solution has at least one of a pH higher than that of the first reference solution by 0.3 or more and an electrical conductivity ½ or less of that of the first reference solution.

According to the present invention, there is also provided a taste measurement method characterized in that the sensor responses are transient responses.

According to the present invention, there is also provided a taste measurement method characterized in that the sensor responses are membrane potentials.

According to the present invention, there is also provided a taste measurement method characterized in that the sensor responses are membrane resistances.

For example, according to the taste measurement method of the present invention, a desired reference solution is prepared. A sensor potential V01 in the first reference solution is measured. After the sensor is dipped in the target measurement solution containing ionic adsorption substances for a predetermined period of time, a sensor potential V02 in the second reference solution is measured. The difference between V01 and V02 is obtained.

According to the taste measurement method of the present invention, the second reference solution is a solution which is less sour or salty than the first reference solution, that is, the second reference solution has at least one of a pH, i.e., hydrogen ion exponent (pH) higher than that of the first reference solution by 0.3 or more and an electrical conductivity ½ or less of that of the first reference solution.

According to the taste measurement method of the present invention, for example, the taste sensor is cleaned before the sensor potential V02 in the second reference solution is measured.

The desired reference solution allows measurement of any target measurement solution if the reference solution does not contain, e.g., ionic adsorption substances.

This is because an ionic adsorption substance is not adsorbed in the molecular film when the taste sensor is dipped in such a reference solution.

Examples of this reference solution are an aqueous solution containing only an acid, an aqueous solution containing only salt, an aqueous solution containing an acid and salt, and aqueous solutions obtained by adding sweet components in the above aqueous solutions.

Ionic adsorption substances identical to that contained in the target measurement solution may be contained in a reference solution in a small amount to the extent that the contents of the ionic adsorption substances do not adversely affect the taste measurement of the target measurement solution.

Even if ionic adsorption substances are adsorbed in the molecular film upon dipping the taste sensor in a reference solution, no problem is posed when the contents of the ionic adsorption substances are negligible as compared with an amount adsorbed when the taste sensor is dipped in the target measurement solution for a predetermined period of time.

According to the above method of the present invention, the sensor potential in the first reference solution is defined as V01, and the sensor potential in the second reference solution upon dipping the sensor in the target measurement solution (sample solution) is defined as V02.

If no ionic adsorption substances adsorptive to the molecular film are present in the sample solution, V02 is almost equal to V01.

For the sake of descriptive simplicity, the first and second reference solutions contain identical components.

If ionic adsorption substances adsorptive to the molecular film are present in the sample solution, the ionic adsorption substances adsorbed on the molecular film serves as a fixed charge in the molecular film.

The membrane potential changes with a change in density of the fixed charge.

The membrane potential of the sensor with adsorption of ionic adsorption substances on the surface of the molecular film dipped in a given reference solution is different from that without adsorption of the ionic adsorption substances on the surface of the molecular film dipped in the given reference solution. Therefore, V01 becomes different from V02.

The difference between V01 and V02 corresponds to the adsorption quantity of the ionic adsorption substances on the film.

If the time of dipping the sensor in the target measurement solution is kept constant, the adsorption quantity of the ionic adsorption substances on the film is proportional to the concentration of the ionic adsorption substances in the target measurement solution. V01 and V02 are measured and the difference between them is calculated. Therefore, information of a taste exhibited by the ionic adsorption substances in the target measurement solution can be obtained from the difference.

If the second reference solution has a lower concentration in taste than the first reference solution, the measurement sensitivity can be increased.

The measurement value difference increases when the second reference solution has a lower concentration in taste than the first reference solution although the differences in adsorption quantities on the film in two sample solution are identical to each other.

If the taste sensor is cleaned prior to the measurement of the sensor potential V02 in the second reference solution, substances adsorbed on the film at strengths having a given level or more can be left adsorbed depending on the strength of cleaning, the type of cleaning solution, and the like. Therefore, the taste information for the remaining adsorption substances can be obtained.

BRIEF DESCRIPTION OF THE DRAWINGS

FIG. 1 is a flow chart showing a measurement sequence according to the first embodiment of the present invention;

FIG. 2 is a flow chart showing a measurement sequence according to the second embodiment of the present invention;

FIG. 3 is a flow chart showing a measurement sequence according to the third embodiment of the present invention;

FIG. 4 is a flow chart showing a measurement sequence according to the fourth embodiment of the present invention;

FIG. 5 is a flow chart showing a measurement sequence according to the fifth embodiment of the present invention;

FIG. 6 is a flow chart showing a measurement sequence according to the sixth embodiment of the present invention;

FIG. 7 is a flow chart showing a measurement sequence according to the seventh embodiment of the present invention;

FIG. 9A is a graph showing (V02j–V01) corresponding to adsorption quantities in order to show the results of sensitivity characteristics of molecular membrane No. 2 (Table 2) for taste-exhibiting substances for the five basic tastes and milk (as the representative of oils and fats) in Table 3;

FIG. 9B is a graph showing the relative values (Vi–V01) using a sensor potential V01 of a reference solution as a reference under the same conditions as in FIG. 9A;

FIG. 10A is a graph showing (V02j–V01) corresponding to adsorption quantities in order to show the results of sensitivity characteristics of molecular film No. 3 (Table 2) for taste-exhibiting substances for the five basic tastes and milk (as the representative of oils and fats) in Table 3;

FIG. 10B is a graph showing the relative values (Vi–V01) using a sensor potential V01 of a reference solution as a reference under the same conditions as in FIG. 10A;

FIG. 20 is a perspective view for explaining the schematic arrangement of a batch type taste recognition system to which the taste measurement method of the present invention is applied;

FIG. 21 is a perspective view showing the detailed structure of a sensor unit in FIG. 20;

FIGS. 22A and 22B are detailed views showing the sensor probe and reference electrode of the sensor unit shown in FIG. 21;

FIG. 23 is a block diagram showing the schematic arrangement of the system shown in FIG. 20;

FIGS. 24A and 24B are perspective views showing the support form of reference solution containers, stabilizing solution containers, cleaning solution containers, measurement solution (sample solution) containers, and the like placed on a container support plate in FIG. 20;

FIG. 25 is a schematic view showing the operation of the system shown in FIG. 20;

FIGS. 27A and 27B are graphs showing the measurement results of beer and green tea according to the method of the present invention; and FIG. 28 is a graph for explaining the principle of the taste measurement method according to the present invention.

BEST MODE OF CARRYING OUT THE INVENTION

Figure 8A:
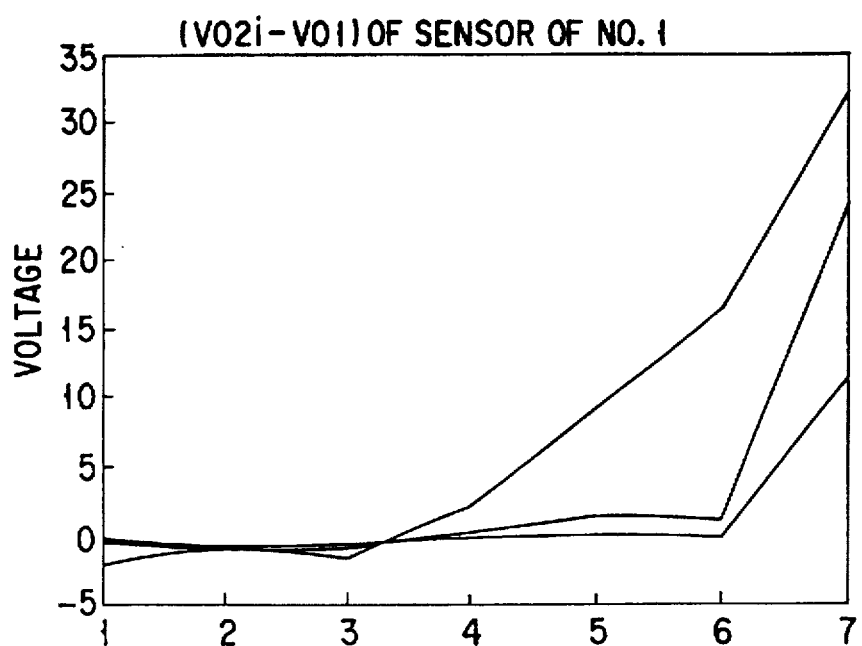
FIG. 8A is a graph showing (V02j–V01) corresponding to adsorption quantities in order to show the results of sensitivity characteristics of molecular film No. 1 (Table 2) for taste-exhibiting substances for the five basic tastes and milk (as the representative of oils and fats) in Table 3.
Figure 8B:
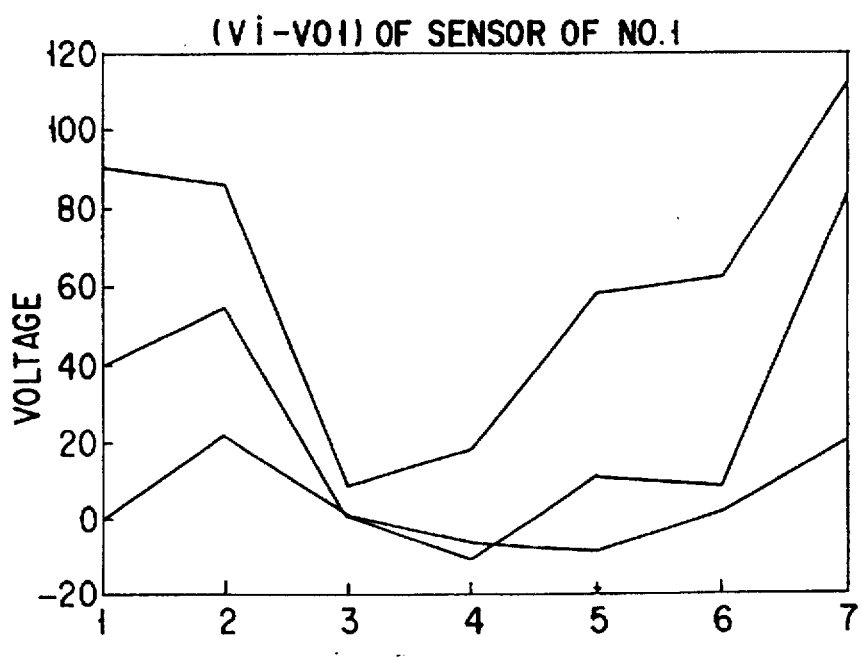
FIG. 8B is a graph showing the relative values (Vi–V01) using a sensor potential V01 of a reference solution as a reference under the same conditions as in FIG. 8A.
Figure 11A:
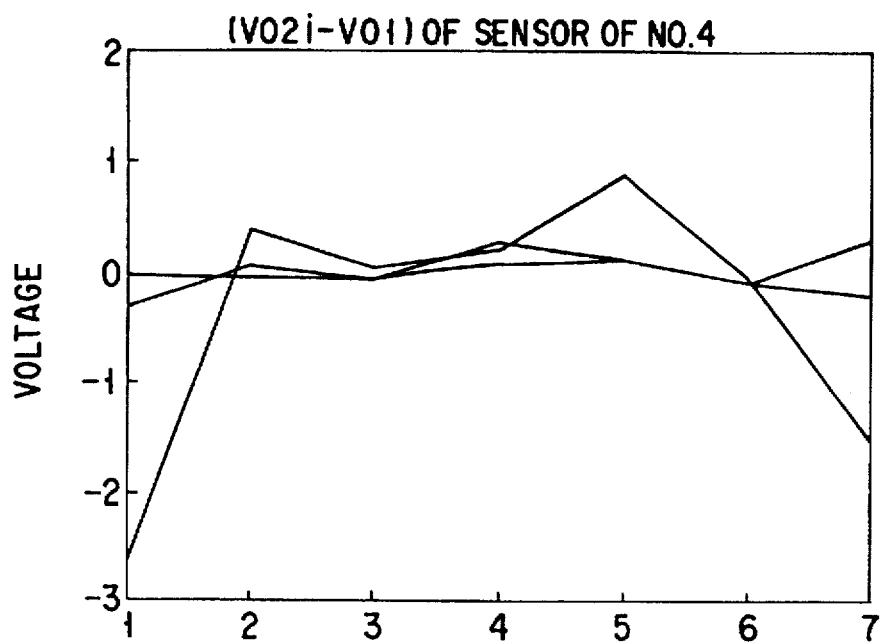
FIG. 11A is a graph showing (V02j–V01) corresponding to adsorption quantities in order to show the results of sensitivity characteristics of molecular film No. 4 (Table 2) for taste-exhibiting substances for the five basic tastes and milk (as the representative of oils and fats) in Table 3.
Figure 11B:
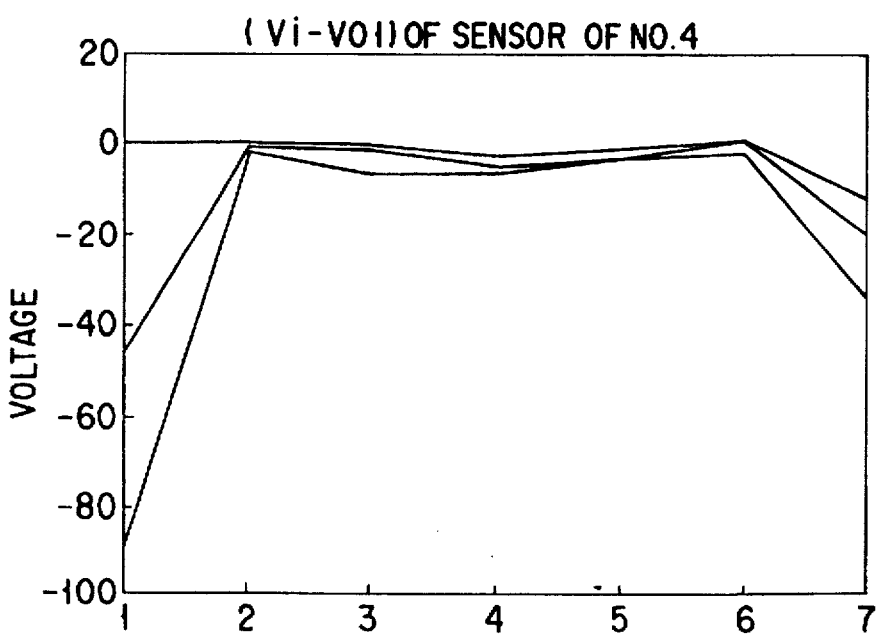
FIG. 11B is a graph showing the relative values (Vi–V01) using a sensor potential V01of a reference solution as a reference under the same conditions as in FIG. 11A.
Figure 12A:
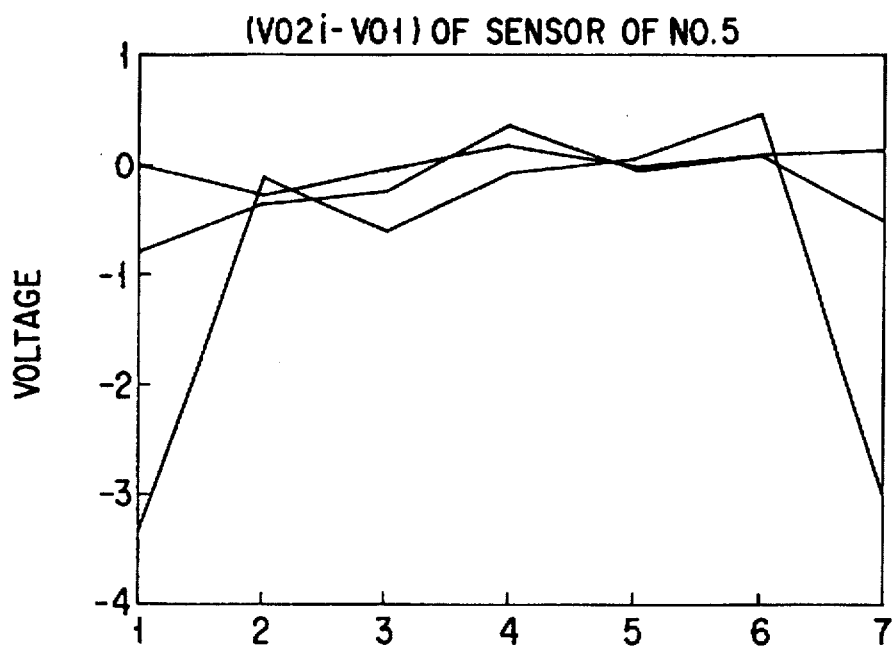
FIG. 12A is a graph showing (V02j–V01) corresponding to adsorption quantities in order to show the results of sensitivity characteristics of molecular film No. 5 (Table 2) for taste-exhibiting substances for the five basic tastes and milk (as the representative of oils and fats) in Table 3.
Figure 12B:
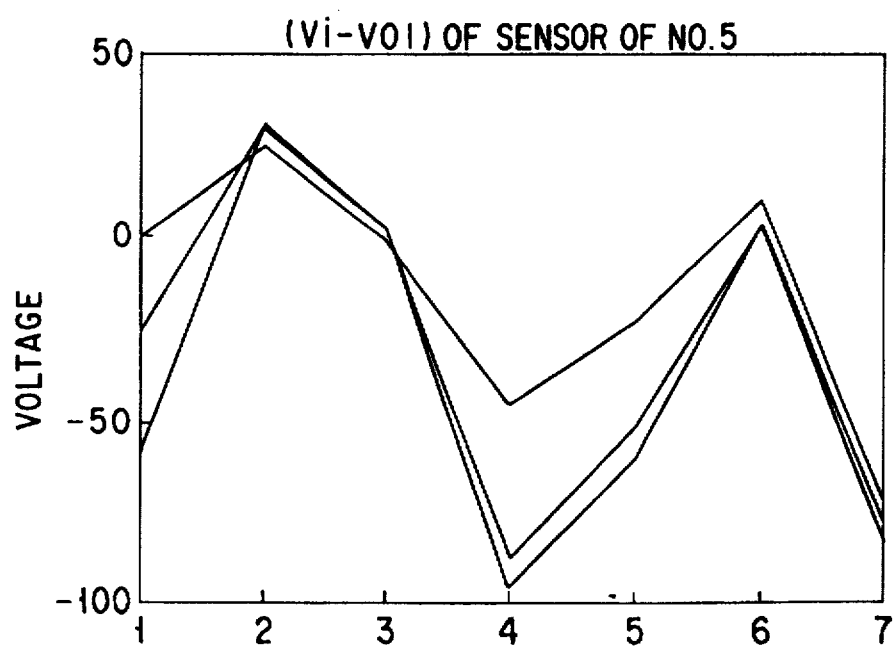
FIG. 12B is a graph showing the relative values (Vi–V01) using a sensor potential V01 of a reference solution as a reference under the same conditions as in FIG. 12A.
Figure 13A:
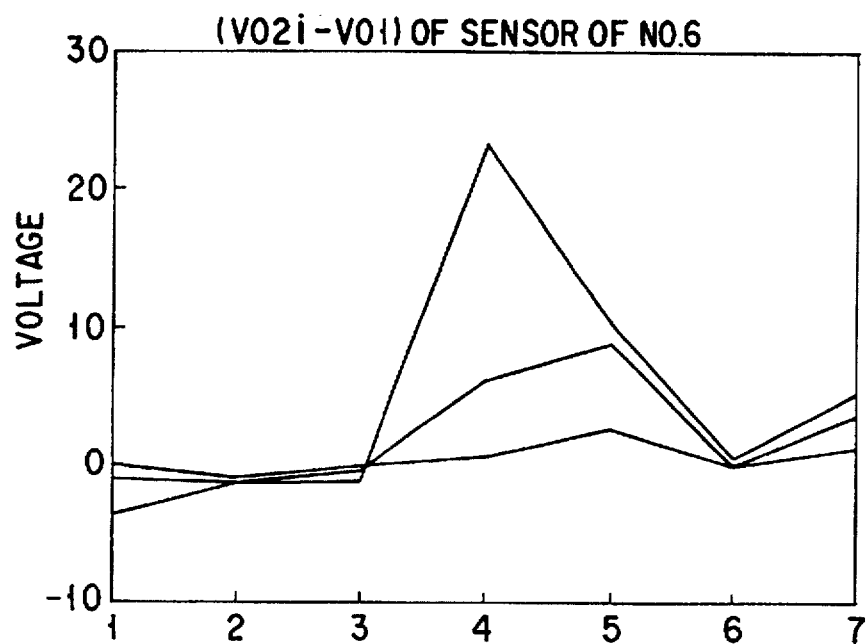
FIG. 13A is a graph showing (V02j–V01) corresponding to adsorption quantities in order to show the results of sensitivity characteristics of molecular film No. 6 (Table 2) for taste-exhibiting substances for the five basic tastes and milk (as the representative of oils and fats) in Table 3.
Figure 13B:
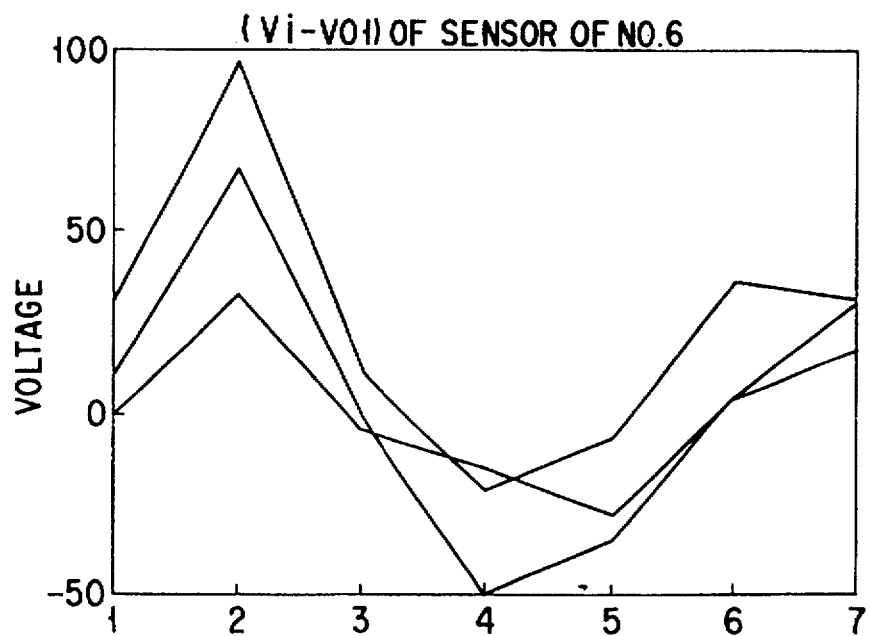
FIG. 13B is a graph showing the relative values (Vi–V01) using a sensor potential V01 of a reference solution as a reference under the same conditions as in FIG. 13A.

A taste recognition system to which a taste measurement method according to the present invention is applied will be generally described below.

A batch type taste recognition system shown in FIGS. 20 to 25 is constituted by a detection unit/handler unit 101 and a data processing unit 102.

As shown in FIG. 20, the detection unit/handler unit 101 has a measurement table 101a, a robot main body 101b, a robot drive unit 101c, and a container support plate 101d.

A sensor unit 101e is mounted at the distal end portion of the robot main body 101b.

As shown in FIG. 21, the sensor unit 101e has a buffer amplifier 101f, a sensor support portion 101g, a sensor guard 101h, a photosensor 101i, a plurality of sensor probes 101j, and a reference electrode 101k.

As shown in FIGS. 22A and 22B, each of the sensor probe 101j and the reference electrode 101k has a probe main body 101l, an electrode terminal 101m, an Ag/AgCl electrode 101n, and an internal solution (saturated AgCl, 3.3M KCl) 101o.

A lipid membrane 101p is formed at the distal end portion of each sensor probe 101j.

A saturated KCl agar 101q is positioned at the distal end portion of the reference electrode 101k.

The data processing unit 102 has a rack main body 102a, a power supply box 102b, a personal computer 102c, an operation unit 102d, and a display unit 102e.

In the batch type taste recognition system having the above configuration, as shown in FIGS. 23 and 25, the robot main body 101b of the detection unit/handler unit 101 dips the sensor unit 101e in the reference solution containers, the stabilizing solution containers, the cleaning solution containers, and the measurement solution (sample solution) containers placed on the container support plate 101d in a predetermined form under the control of the personal computer 102c, thereby performing automatic measurements, as shown in FIGS. 24A and 24B.

The data processing unit 102 A/D-converts data from the sensor unit 101e and fetches the digital data to the personal computer, thereby performing principal component analysis and the like. The data processing unit 102 performs final taste recognition of the sample solutions and outputs their taste information.

Figure 26:
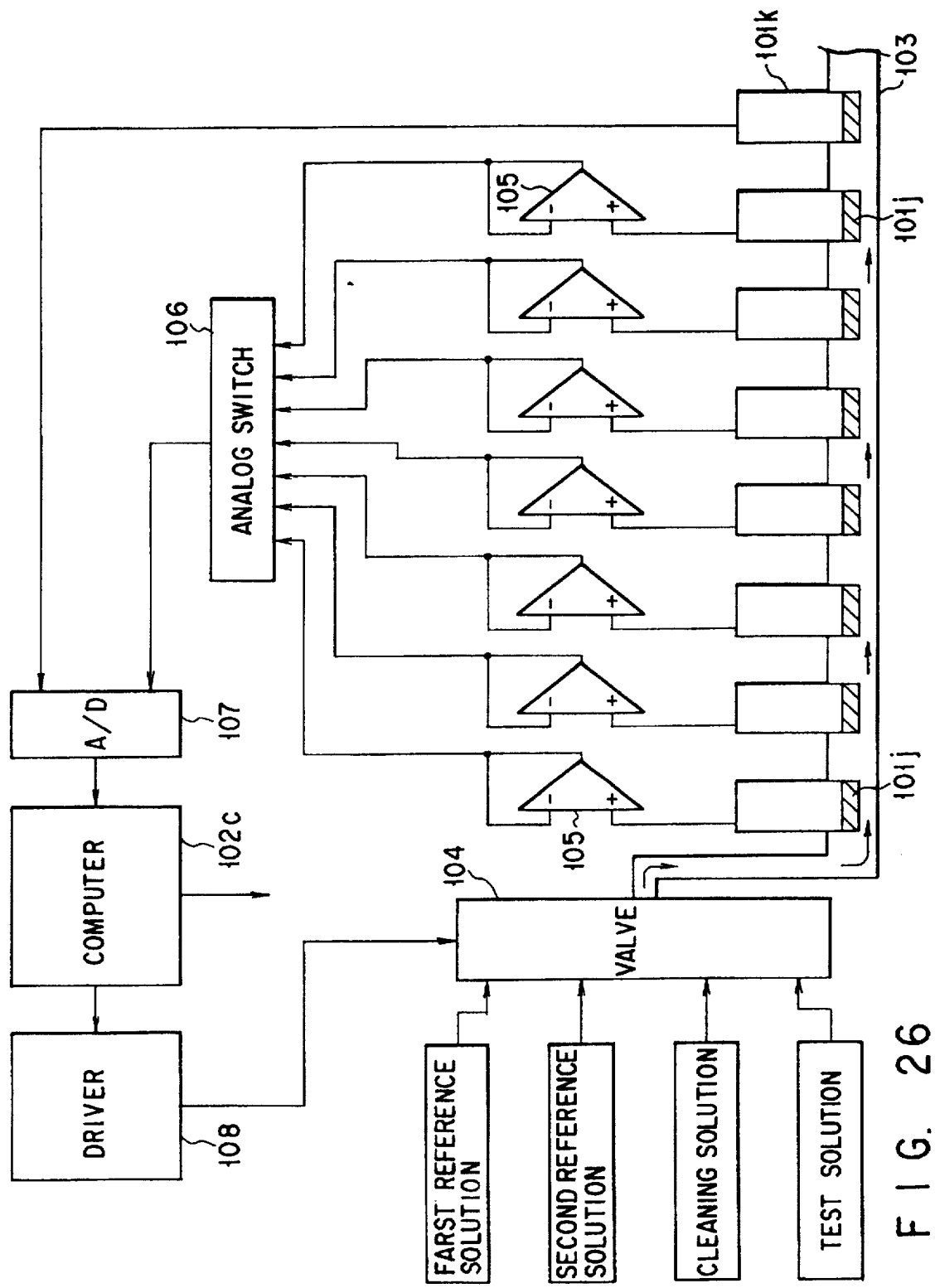
FIG. 26 is a block diagram showing the schematic arrangement of a flow type taste recognition system to which the taste measurement method of the present invention is applied.

In a flow type (automation line scheme) taste recognition system shown in FIG. 26, the plurality of sensor probes 101j and the reference electrode 101k are disposed in a pipe 103.

A reference solution, a cleaning solution, a measurement solution (sample solution) or the like is switched by a valve 104 and is supplied to the pipe 103 through a pump (not shown).

Data from the plurality of sensor probes 101j are subjected to impedance conversion by amplifiers 105 in film potential measurement. The outputs from the amplifiers 105 are sampled by an analog switch 106. The sampling result is A/D-converted by an A/D converter 107 together with the data from the reference electrode 101k. The outputs from the A/D converter 107 are fetched by the personal computer 102c.

The personal computer 102c performs principal component analysis and the like of the fetched data as in the batch type. The personal computer 102c performs final taste recognition of the sample solution and outputs its taste information.

Switching and control of the valve 104 and the pump (not shown) are performed by a driver 108 controlled by the personal computer 102c.

The embodiments of the present invention based on the above general description will be described with reference to the accompanying drawings.

FIG. 1 is a flow chart showing a measurement sequence according to the first embodiment of the present invention.

The first embodiment of the present invention will be described with reference to FIG. 1.

In this embodiment, the first and second reference solutions are identical to each other.

The identical solutions may be obtained by commonly using a reference solution in a single container or using reference solutions having identical components in different containers.

Step S1: A sensor potential V01 of a (first) reference solution is measured.

In batch type measurement (a measurement scheme in which a target measurement solution is sampled in a container such as a beaker, as shown in, e.g., FIGS. 20 to 25), a taste sensor is repeatedly dipped in a reference solution and removed from it into air a predetermined number of times, and the sensor potential V01 in the reference solution is measured again.

In flow type measurement (a measurement scheme in which a target measurement solution and a reference solution are selectively flowed to the measurement pipe in which taste sensors are set, as shown in, e.g., FIG. 26), after the reference solution is flowed to the taste sensor for a predetermined period of time, the sensor potential V01 in the reference solution is measured again.

Step S2: The immediately preceding sensor potential V01 in the reference solution is compared with the current sensor potential V01 in the reference solution. If the range of changes falls within a preset value, the sensor is regarded to have been stabilized. The flow advances to step S3 to measure the sensor potential in a sample. If the range of changes, however, falls outside the preset value, the flow returns to step S1.

This indicates that the influences of dipping/removal of the sensor and the flow of the measurement solution are checked, and dipping/removal of the sensor and the flow of the measurement solution are periodically performed until the influences are eliminated.

The finally stabilized sensor potential in the reference solution is defined as V01.

Step S3: When the sensor potential is stabilized, the sensor is dipped in a sample (target measurement solution) Si for a predetermined period of time, and at the same time, a sensor potential Vi of the sample Si is measured.

The predetermined dipping time is determined to attain uniform adsorption conditions of the respective samples Si.

Step S4: A measurement result $\Delta Vi=Vi-V01$ of the sample Si is calculated.

Step S6: A sensor potential V02i of a (second) reference solution is measured.

Step S7: A measurement result $\Delta Vki=V02i-V01$ of the sample Si is calculated.

Step S8: The sensor is cleaned.

As practical cleaning, the sensor is dipped and moved in a cleaning solution or dipped and removed in the cleaning solution in, e.g., a batch type.

When the next sample is to be measured, the flow returns to step S1.

FIG. 2 is a flow chart showing a measurement sequence according to the second embodiment of the present invention.

The second embodiment will be described with reference to FIG. 2.

In this embodiment, the second reference solution is set to have a lower concentration in taste than the first reference solution to increase the measurement sensitivity.

Step S1: A sensor potential V01 of the first reference solution is measured.

In batch type measurement, a taste sensor is repeatedly dipped in a reference solution and removed from it into air a predetermined number of times, and the sensor potential V01 in the reference solution is measured again.

In flow type measurement, after the reference solution is flowed to the taste sensor for a predetermined period of time, the sensor potential V01 in the reference solution is measured again.

Step S2: The immediately preceding sensor potential V01 in the reference solution is compared with the current sensor potential V01 in the reference solution. If the range of changes falls within a preset value, the sensor is regarded to have been stabilized. The flow advances to step S3 to measure the sensor potential in a sample. If the range of changes, however, falls outside the preset value, the flow returns to step S1.

This indicates that the influences of dipping/removal of the sensor and the flow of the measurement solution are checked, and dipping/removal of the sensor and the flow of the measurement solution are periodically performed until the influences are eliminated.

The finally stabilized sensor potential in the reference solution is defined as V01.

Step S3: When the sensor potential is stabilized, the sensor is dipped in a sample Si for a predetermined period of time, and at the same time, a sensor potential Vi of the sample Si is measured.

Step S4: A measurement result $\Delta Vi=Vi-V01$ of the sample Si is calculated.

Step S6: A sensor potential V02i of the second reference solution is measured.

Step S7: A measurement result $\Delta Vki=V02i-V01$ of the sample Si is calculated.

Step S8: The sensor is cleaned.

When the next sample is to be measured, the flow returns to step S1.

FIG. 3 is a flow chart showing a measurement sequence according to the third embodiment of the present invention.

The third embodiment of the present invention will be described with reference to FIG. 3.

In this embodiment, the first and second reference solutions are identical to each other.

Step S1: A sensor potential V01 of a (first) reference solution is measured.

In batch type measurement, a taste sensor is repeatedly dipped in a reference solution and removed from it into air a predetermined number of times, and the sensor potential V01 in the reference solution is measured again.

In flow type measurement, after the reference solution is flowed to the taste sensor for a pre-determined period of time, the sensor potential V01 in the reference solution is measured again.

Step S2: The immediately preceding sensor potential V01 in the reference solution is compared with the current sensor potential V01 in the reference solution. If the range of changes falls within a preset value, the sensor is regarded to have been stabilized. The flow advances to step S3 to measure the sensor potential in a sample. If the range of changes, however, falls outside the preset value, the flow returns to step S1.

This indicates that the influences of dipping/removal of the sensor and the flow of the measurement solution are checked, and dipping/removal of the sensor and the flow of the measurement solution are periodically performed until the influences are eliminated.

The finally stabilized sensor potential in the reference solution is defined as V01.

Step S3: When the sensor potential is stabilized, the sensor is dipped in a sample Si for a predetermined period of time, and at the same time, a sensor potential Vi of the sample Si is measured.

Step S4: A measurement result $\Delta Vi=Vi-V01$ of the sample Si is calculated.

Step S5: The sensor is cleaned.

In this case, the sensor is cleaned with a certain strength, and substances having adsorption powers which withstand this strength of cleaning are left.

Step S6: A sensor potential V02i of a (second) reference solution is measured.

Step S7: A measurement result $\Delta Vki=V02i-V01$ of the sample Si is calculated.

Step S8: The sensor is cleaned.

When the next sample is to be measured, the flow returns to step S1.

In each of the first to third embodiments, the sensor is dipped in the sample Si and at the same time the sensor potential Vi of the sample Si is measured in step S3. In step S4, the measurement result $\Delta Vi=Vi-V01$ of the sample Si is calculated.

The measurement result $\Delta Vi$ is a relative value of the sample Si with reference to V01 and indicates the overall taste of the sample Si in addition to the taste resulting from the adsorption substance when viewed from the sensor.

In each of the fourth to sixth embodiments to be described below, a sensor is dipped in a sample Si for a predetermined period of time in step S3'.

The measurement is therefore performed for only the taste of the adsorption substance of the sample Si.

FIG. 4 is a flow chart showing a measurement sequence according to the fourth embodiment of the present invention.

The fourth embodiment of the present invention will be described with reference to FIG. 4.

In this embodiment, the first and second reference solutions are identical to each other.

Step S1: A sensor potential V01 of a (first) reference solution is measured.

In batch type measurement, a taste sensor is repeatedly dipped in a reference solution and removed from it into air a predetermined number of times, and the sensor potential V01 in the reference solution is measured again.

In flow type measurement, after the reference solution is flowed to the taste sensor for a predetermined period of time, the sensor potential V01 in the reference solution is measured again.

Step S2: The immediately preceding sensor potential V01 in the reference solution is compared with the current sensor potential V01 in the reference solution. If the range of changes falls within a preset value, the sensor is regarded to have been stabilized. The flow advances to step S3' to measure the sensor potential in a sample. If the range of changes, however, falls outside the preset value, the flow returns to step S1.

This indicates that the influences of dipping/removal of the sensor and the flow of the measurement solution are checked, and dipping/removal of the sensor and the flow of the measurement solution are periodically performed until the influences are eliminated.

The finally stabilized sensor potential in the reference solution is defined as V01.

Step S3': The sensor is dipped in the sample (target measurement solution) Si for a predetermined period of time.

Step S6: A sensor potential V02i of a (second) reference solution is measured.

Step S7: A measurement result $\Delta Vki=V02i-V01$ of the sample Si is calculated.

Step S8: The sensor is cleaned.

As practical cleaning, the sensor is dipped and moved in a cleaning solution or dipped and removed in the cleaning solution in, e.g., a batch type.

When the next sample is to be measured, the flow returns to step S1.

FIG. 5 is a flow chart showing a measurement sequence according to the fifth embodiment of the present invention.

The fifth embodiment will be described with reference to FIG. 5.

In this embodiment, the second reference solution is set to have a lower concentration in taste than the first reference solution to increase the measurement sensitivity.

Step S1: A sensor potential V01 of the first reference solution is measured.

In batch type measurement, a taste sensor is repeatedly dipped in a reference solution and removed from it into air a predetermined number of times, and the sensor potential V01 in the reference solution is measured again.

In flow type measurement, after the reference solution is flowed to the taste sensor for a predetermined period of time, the sensor potential V01 in the reference solution is measured again.

Step S2: The immediately preceding sensor potential V01 in the reference solution is compared with the current sensor potential V01 in the reference solution. If the range of changes falls within a preset value, the sensor is regarded to have been stabilized. The flow advances to step S3' to measure the sensor potential in a sample.

If the range of changes, however, falls outside the preset value, the flow returns to step S1.

This indicates that the influences of dipping/removal of the sensor and the flow of the measurement solution are checked, and dipping/removal of the sensor and the flow of the measurement solution are periodically performed until the influences are eliminated.

The finally stabilized sensor potential in the reference solution is defined as V01.

Step S3': The sensor is dipped in the sample (target measurement solution) Si for a predetermined period of time.

Step S6: A sensor potential V02i of the second reference solution is measured.

Step S7: A measurement result $\Delta Vki=V02i-V01$ of the sample Si is calculated.

Step S8: The sensor is cleaned.

When the next sample is to be measured, the flow returns to step S1.

FIG. 6 is a flow chart showing a measurement sequence according to the sixth embodiment of the present invention.

The sixth embodiment of the present invention will be described with reference to FIG. 6.

In this embodiment, the first and second reference solutions are identical to each other.

Step S1: A sensor potential V01 of a (first) reference solution is measured.

In batch type measurement, a taste sensor is repeatedly dipped in a reference solution and removed from it into air a predetermined number of times, and the sensor potential V01 in the reference solution is measured again.

In flow type measurement, after the reference solution is flowed to the taste sensor for a predetermined period of time, the sensor potential V01 in the reference solution is measured again.

Step S2: The immediately preceding sensor potential V01 in the reference solution is compared with the current sensor potential V01 in the reference solution. If the range of changes falls within a preset value, the sensor is regarded to have been stabilized. The flow advances to step S3' to measure the sensor potential in a sample. If the range of changes, however, falls outside the preset value, the flow returns to step S1.

This indicates that the influences of dipping/removal of the sensor and the flow of the measurement solution are checked, and dipping/removal of the sensor and the flow of the measurement solution are periodically performed until the influences are eliminated.

The finally stabilized sensor potential in the reference solution is defined as V01.

Step S3': The sensor is dipped in the sample (target measurement solution) Si for a predetermined period of time.

Step S5: The sensor is cleaned.

In this case, the sensor is cleaned with a certain strength, and substances having adsorption powers which withstand this strength of cleaning are left.

Step S6: A sensor potential V02i of a (second) reference solution is measured.

Step S7: A measurement result $\Delta Vki=V02i-V01$ of the sample Si is calculated.

Step S8: The sensor is cleaned.

When the next sample is to be measured, the flow returns to step S1.

FIG. 7 is a flow chart showing a measurement sequence according to the seventh embodiment of the present invention.

The seventh embodiment will be described with reference to FIG. 7.

In this embodiment, the first reference solution itself also serves as a sensor cleaning solution.

Step S1: A sensor potential V01 in the first reference solution is measured, and at the same time, the sensor is cleaned.

In batch type measurement, a taste sensor is repeatedly dipped in a reference solution and removed from it into air a predetermined number of times, and the sensor potential V01 in the reference solution is measured again.

In flow type measurement, after the reference solution is flowed to the taste sensor for a predetermined period of time, the sensor potential V01 in the reference solution is measured again.

Step S2: The immediately preceding sensor potential V01 in the reference solution is compared with the current sensor potential V01 in the reference solution. If the range of changes falls within a preset value, the sensor is regarded to have been stabilized. The flow advances to step S3 to measure the sensor potential in a sample. If the range of changes, however, falls outside the preset value, the flow returns to step S1.

This has two meanings. First, this indicates that the influences of dipping/removal of the sensor and the flow of the measurement solution are checked, and dipping/removal of the sensor and the flow of the measurement solution are periodically performed until the influences are eliminated.

Second, it is checked if the membrane surface is refreshed by the cleaning solution and set in a steady state.

The finally stabilized sensor potential in the reference solution is defined as V01.

Step S3: When the sensor potential is stabilized, a sensor potential Vi of the sample Si is measured.

Step S4: A measurement result $\Delta Vi=Vi-V01$ of the sample Si is calculated.

Step S6: A sensor potential V02i of the second reference solution is measured.

Step S7: A measurement result $\Delta Vki=V02i-V01$ of the sample Si is calculated.

When the next sample is to be measured, the flow returns to step S1.

In each embodiment described above, the following process may be performed.

(1) The check for stability of the sensor in reference solution A may be performed once for every several samples.

(2) In the check for stability of the sensor in reference solution A, when the stability is poor, the flow may return to the cleaning process (first to sixth embodiments).

(3) "Co-washing" may be performed in each solution prior to measurements in the sample, the first reference solution, and the second reference solution.

In this case, since the first reference solution also serves as the cleaning solution in the seventh embodiment, "co-washing" also serves as the cleaning process.

(4) Since different cleaning methods are employed depending on the types of sensors and the types of adsorption substances, different cleaning processes are performed.

The cleaning process may be a combination of various cleaning processes.

The results of sensitivity characteristics of taste-exhibiting substances for the five basic tastes and milk (as the representative of oils and fats) in Table 3 are shown in FIGS. 8A and 8B to 13A and 13B.

Each molecular film uses a lipid material listed in Table 1, and Nos. 1 to 6 in Table 2 correspond to FIGS. 8A and 8B to 13A and 13B, respectively.

TABLE 2

| No. | Lipid |
| --- | --- |
| 1 | dioctyl phosphate |
| 2 | oleic acid |
| 3 | lecithin |
| 4 | trioctylmethyl ammonium chloride |
| 5 | oleyl amine |
| 6 | mixture of Nos. 1 and 4 |

The measurement sequence follows the same procedures as in the first embodiment (FIG. 1).

Briefly speaking, the sensor is stabilized in a reference solution (V01), a sample is measured (Vi), co-washing is performed in the same reference solution as described above by dipping and removing the sensor from the reference solution five times, and the potential in the reference solution is measured (V02i).

The dipping time of the film in each of the reference solution and the sample is 30 seconds.

10 mM (mmol) of NaCl are commonly added to each basic taste substance solution, and the concentrations are set in three levels within the range of human tastes, as shown in Table 3.

The reference solution is a solution containing 100 mM of NaCl and 1 mM of tartaric acid. Each cleaning solution except for that of film No. 2 is a solution containing 100 mM of HCl and 40% of ethanol. A cleaning solution for film No. 2 is a 40% ethanol solution.

TABLE 3

| No. | 1 | 2 | 3 | 4 | 5 | 6 | 7 |
|---|---|---|---|---|---|---|---|
| Taste Substance | NaCl | Tartaric Acid | Sucrose | IMP | MSG | Quinine | Milk |
| Concentration 1 | 10 mM | 0.3 mM | 10 mM | 0.3 mM | 3 mM | 0.01 mM | 1/100 diluted |
| Concentration 2 | 100 mM | 3 mM | 100 mM | 8 mM | 30 mM | 0.1 mM | 1/10 diluted |
| Concentration 3 | 1000 mM | 30 mM | 1000 mM | 30 mM | 300 mM | 1 mM | 1/1 diluted |

In Table 3, all the samples except for NaCl commonly contain 10 mM of NaCl each.

In FIGS. 8A and 8B to 13A and 13B, the values of ($V02i$–$V01$) corresponding to adsorption quantities are shown in FIGS. 8A, 9A, 10A, 11A, 12A, and 13A, and the relative values ($Vi$–$V01$) using the sensor potential $V01$ of the reference solution as a reference are shown in FIGS. 8B, 9B, 10B, 11B, 12B, and 13B.

Numerals 1 to 7 along the abscissa of each graph of FIGS. 8A to 13B correspond to taste substance 1, i.e., NaCl to taste substance 7, i.e., milk in Table 3.

In each of FIGS. 8A and 8B to 13A and 13B, the sensitivity of each taste substance is indicated using the value for 10 mM of NaCl as 0.

In measurement, the reference solution may contain 10 mM of NaCl. Since some samples have concentrations much higher than 10 mM of NaCl, as shown in Table 3, and this degrades measurement accuracy, the reference solution is a solution mixture of salt and an acid and set to have an intermediate concentration among samples.

The relative value and adsorption quantity of a reference sample containing 10 mM of NaCl are measured using the reference solution and are subtracted from the relative value and adsorption quantity of each sample, and the differences are shown in each of FIGS. 8A and 8B to 13A and 13B.

In each of FIGS. 8A and 8B to 13A and 13B, almost all the films tend to react with almost all the substances, judging from the relative values. As far as the adsorption quantities are concerned, the molecular films have specific sensitivities to umami of IMP (sodium inosinate) and MSG, i.e., monosodium glutaminate, bitterness of quinine, and milk.

The relative values of the membrane potentials are influenced by both adsorptive and non-adsorptive substances. According to the method of the present invention, only adsorptive substances are detected. By using both of the relative values and the absorption quantities, the adsorptive and non-adsorptive substances can be separated from each other.

For example, in the analysis of soup, it is important to analyze the quality and quantity of an umami substance. The salt concentration is not so important.

Different soups have large differences in salt concentration. The relative values of the sensors are influenced by the large differences in salt concentration. However, the adsorption quantity is not influenced by the differences in salt concentration. For this reason, it is very effective to measure the adsorption quantities in the analysis of soups.

In particular, the adsorption quantity of film No. 6 has sensitivities to only IMP and MSG. This is very effective in the analysis of umami.

The principal component analysis results of the measurement results of Japanese saki are shown in FIGS. 14, 15A, 15B, and 16A to 16E.

The substances of molecular films used are listed in Table 2.

The measurement method follows the same procedures as in the first embodiment (FIG. 1).

The reference solution is a solution consisting of 30 mM of NaCl, 3 mM of succinic acid, and 15% of ethanol. A cleaning solution for films except for films Nos. 1 and 6 is a solution obtaining by replacing 15% of ethanol of the above-mentioned reference solution with 40% of ethanol. A cleaning solution for films Nos. 1 and 6 is a solution containing the components of the above-mentioned cleaning solution and 100 mM of HCl.

Figure 14:
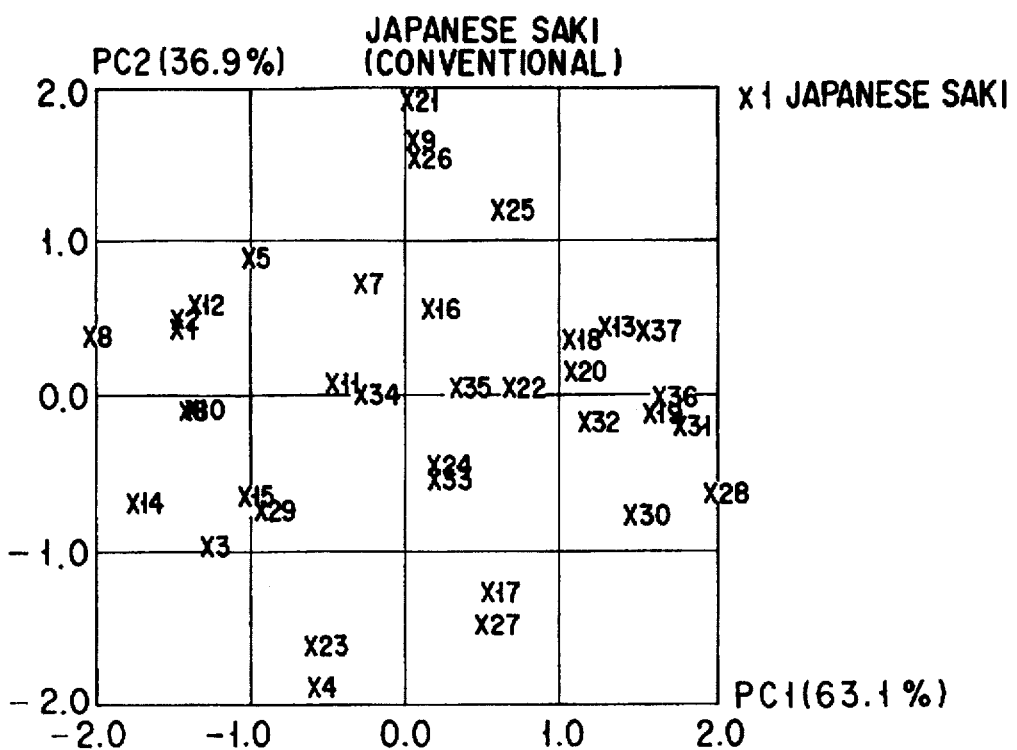
FIG. 14 is a graph showing the results obtained when the major components of Japanese saki are analyzed from its measurement results according to a conventional method.
Figure 16A:
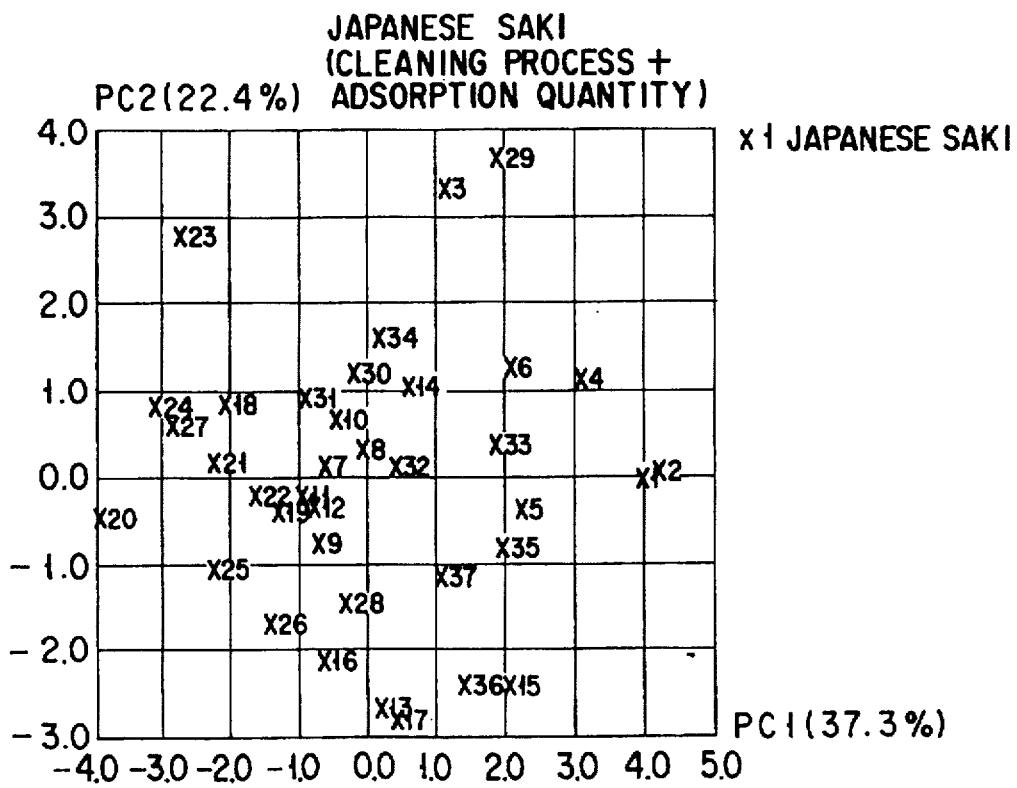
FIGS. 16A, 16B, 16C, 16D and 16E are graphs showing results obtained when the major components of Japanese saki are analyzed from its measurement results according to a method of the present invention.

FIG. 14 shows a case using a conventional method in which a sensor is dipped in pure Japanese saki in advance for a week (the outputs are relative values).

Figure 15A:
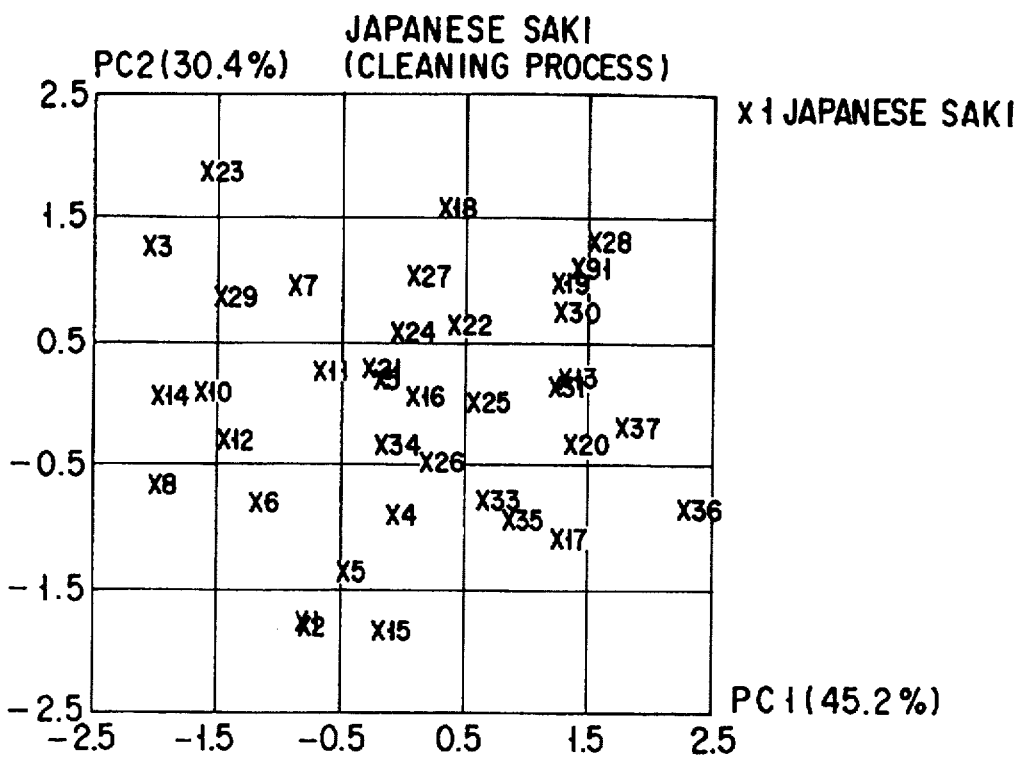
FIGS. 15A and 15B are graphs showing the results obtained when the major components of Japanese saki are analyzed by a method of removing adsorption substances by sensor cleaning in every measurement.
Figure 15B:
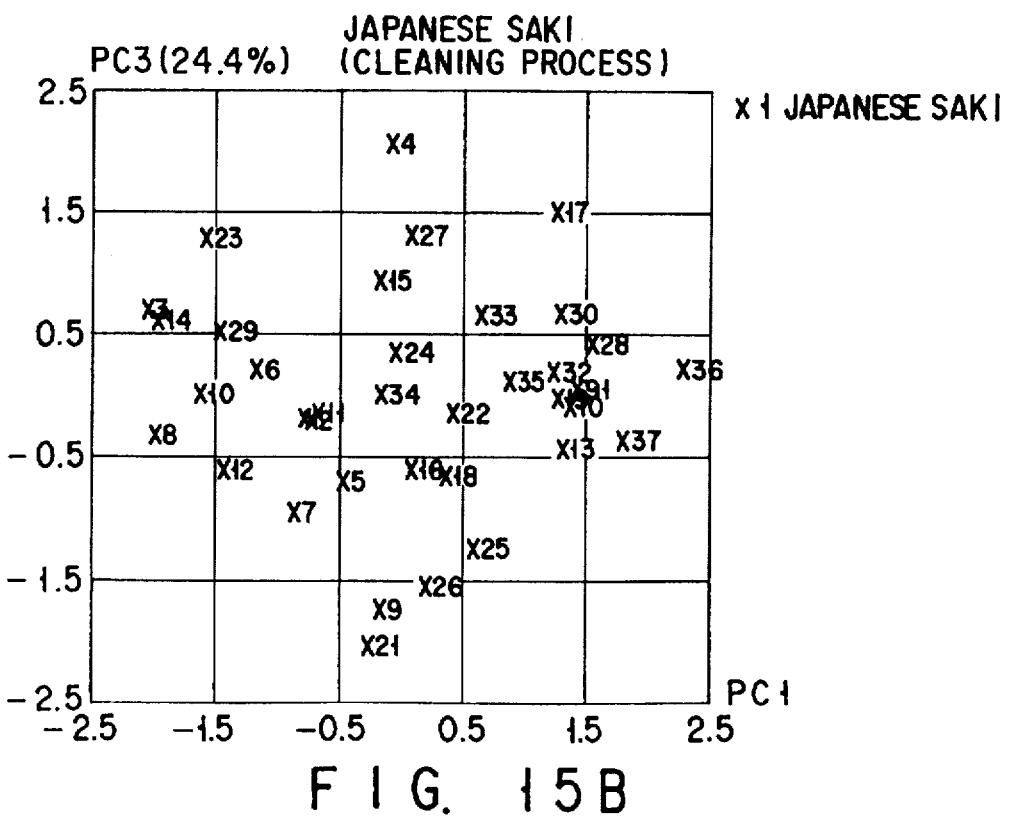
Figure 16B:
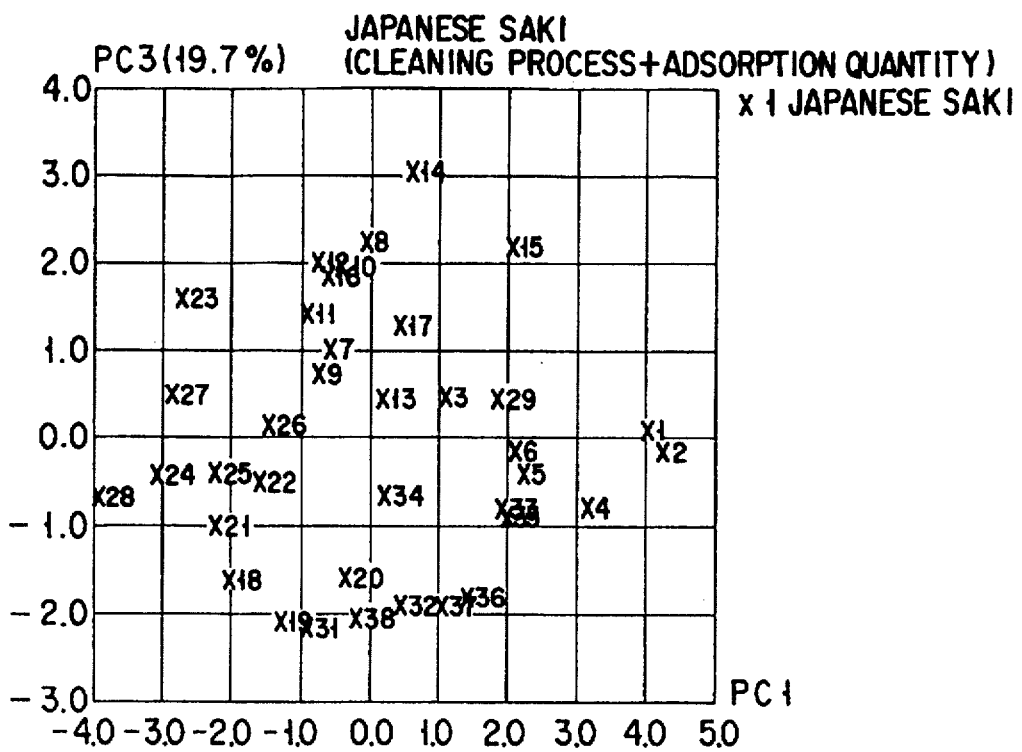
Figure 16C:
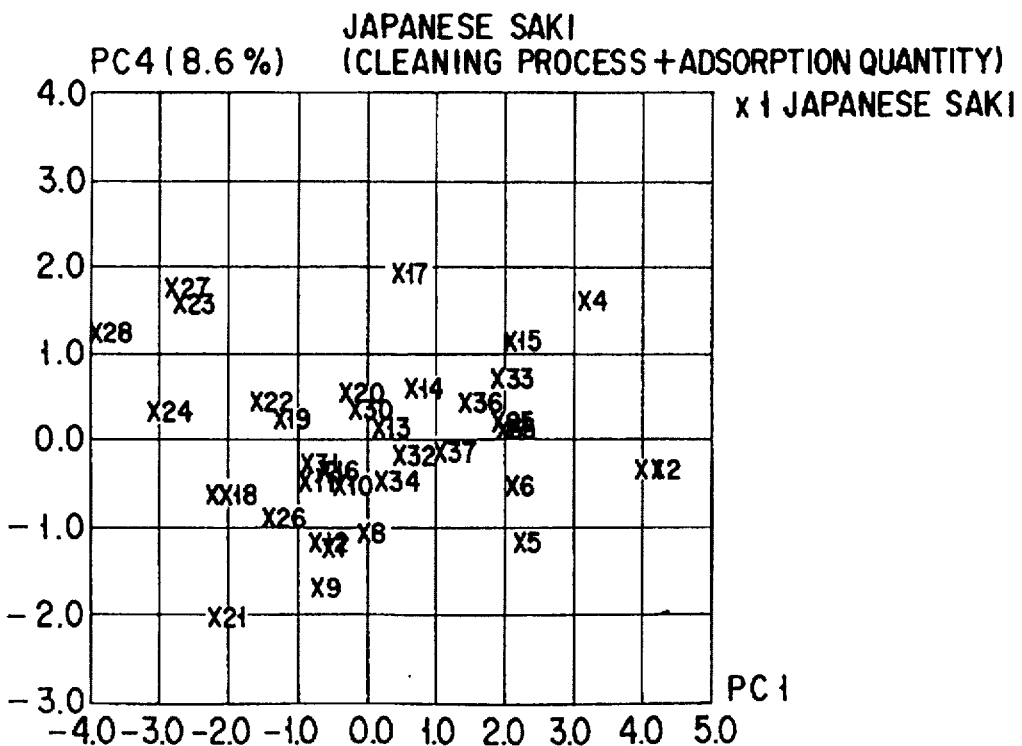
Figure 16D:
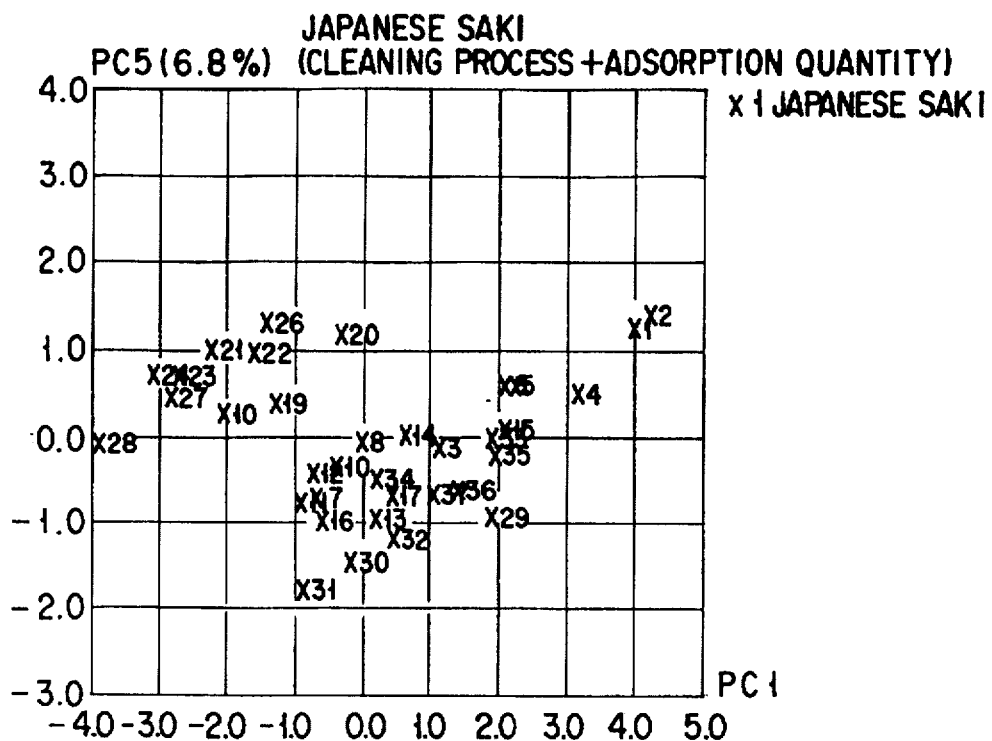
Figure 16E:
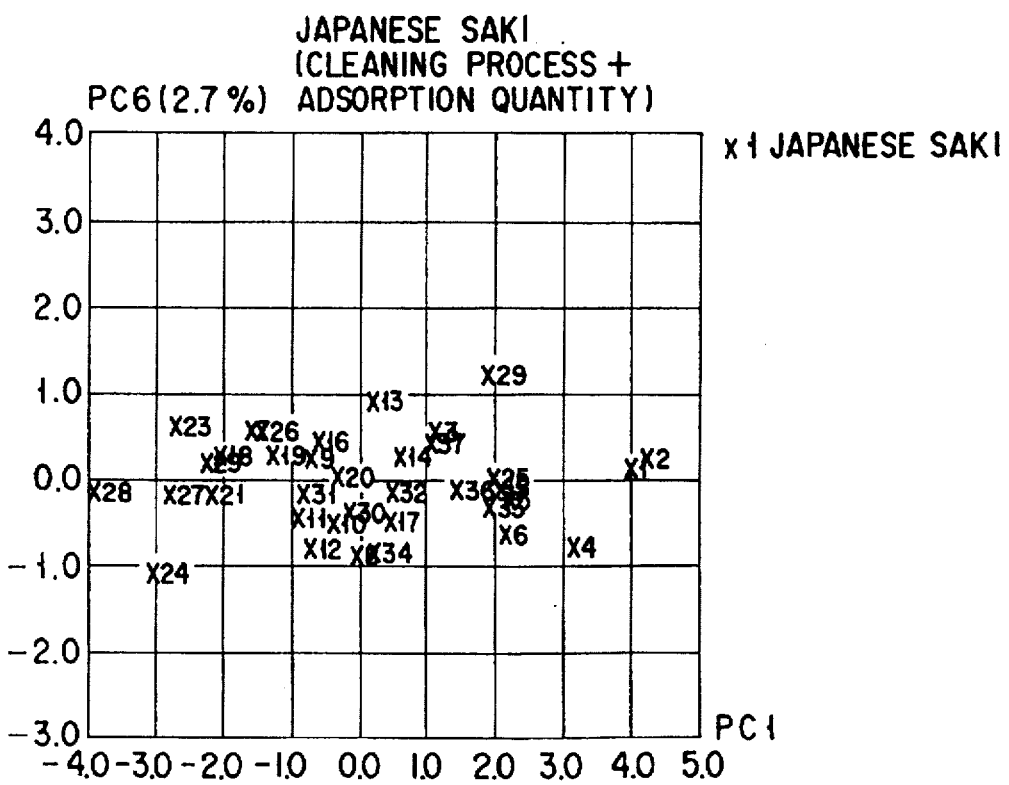
Figure 17:
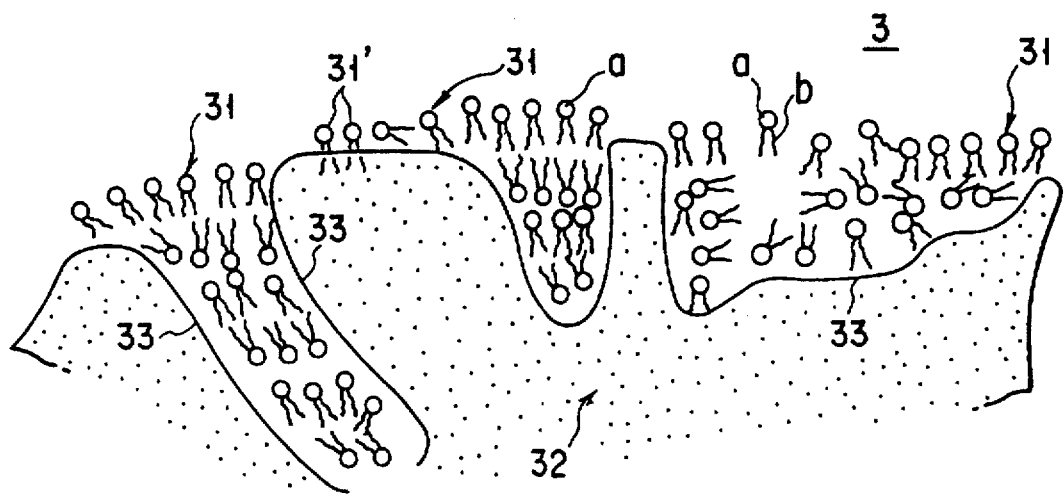
FIG. 17 is a view illustrating a lipid membrane by an expression method used in a chemical design method.
Figure 18A:
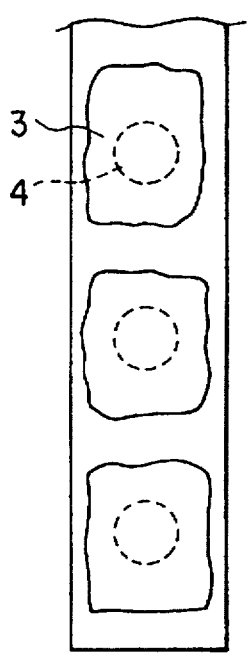
FIGS. 18A and 18B are a front view and a sectional view, respectively, illustrating a taste sensor.
Figure 18B:
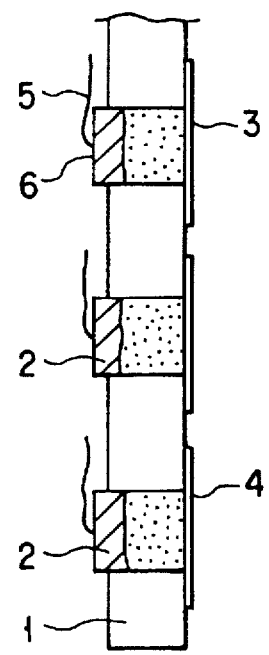
Figure 19:
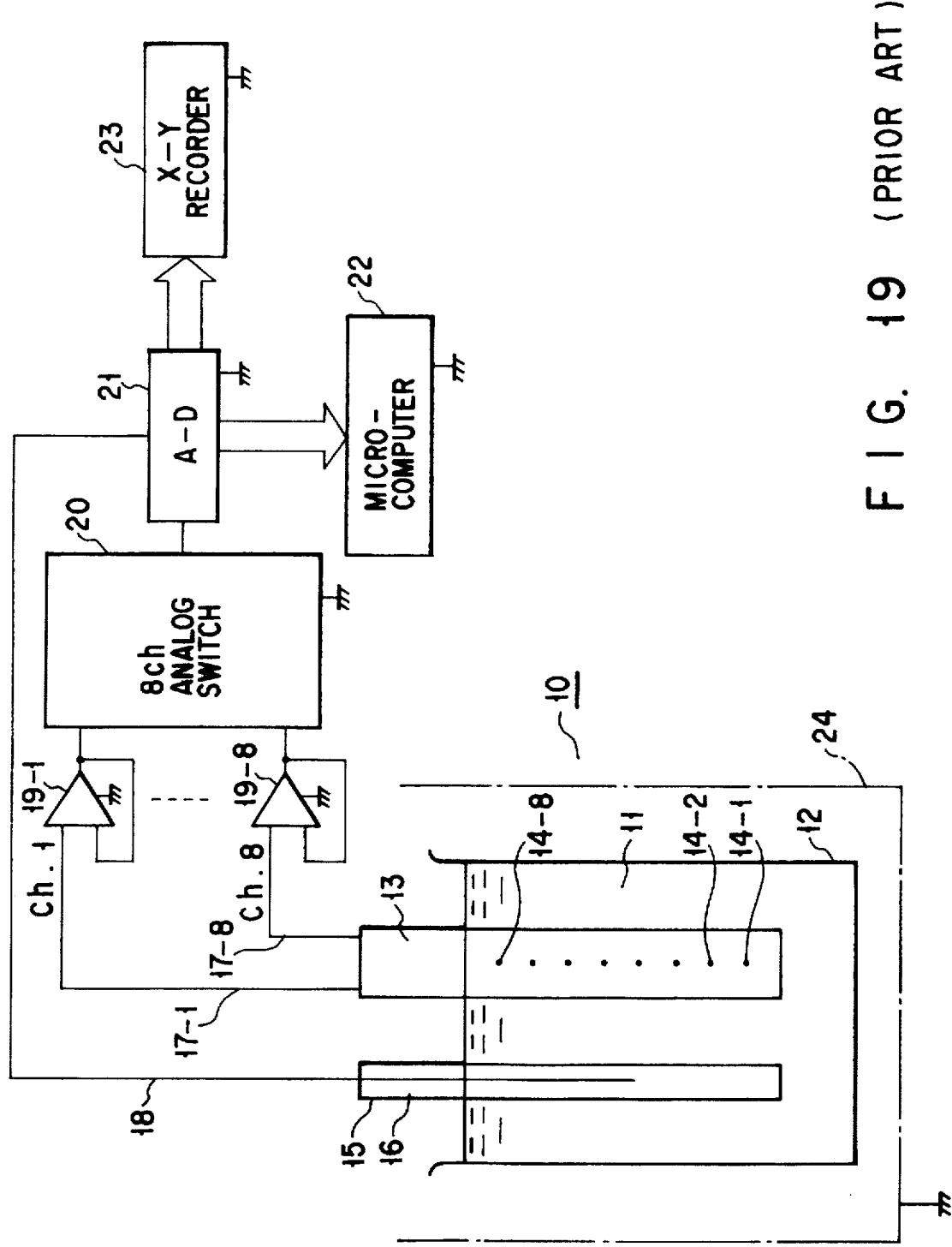
FIG. 19 is a view showing a conventional taste measurement system.

FIGS. 15A and 15B show the relative values obtained by a method of removing adsorption substances by cleaning the sensors in every measurement.

FIGS. 16A to 16E show both the relative values and the adsorption quantities which are obtained upon cleaning of the sensors.

The conventional method (FIG. 14) provides only two-dimensional information (no information from the third principal component). When cleaning is performed (FIGS. 15A and 15B), three-dimensional information (no information from the fourth principal component) can be obtained. When the adsorption quantity information is also used (FIGS. 16A to 16E), six-dimensional information can be obtained. As compared with the conventional method, the information quantity greatly increased.

The differences in tastes which cannot be discriminated from each other by the conventional method can be analyzed in detail according to the method of the present invention.

For example, samples "13" and "37" in FIGS. 14, 15A, 15B, and 16A to 16E have no difference according to the conventional method (FIG. 14). These samples have no difference in relative values (FIGS. 15A and 15B) obtained upon cleaning. However, when the adsorption quantities are considered (FIGS. 16A to 16E), these samples have a difference, as can be apparent from FIG. 16A or 16B.

It is determined that samples "13" and "37" have a difference in adsorption substance.

As described above, according to the present invention, desired reference solutions are prepared. A sensor potential $V01$ in the first reference solution is measured. The sensor is dipped in a target measurement solution containing ionic adsorption substances for a predetermined period of time, and then a sensor potential V02 in the second reference solution is measured. The difference between the sensor potentials V01 and V02 is obtained.

In addition, according to the present invention, the second reference solution is a solution less at least one of sour and salty than the first reference solution, or a solution less both of the sour and salty than the first reference solution.

The taste sensor is washed to a desired degree prior to the measurement of the sensor potential V02 in the second reference solution.

Since the present invention provides the above taste measurement method, (1) the sensitivity associated with a highly adsorptive taste-exhibiting substance such as a bitter substance increases, and (2) the response to a taste component corresponding to an adsorptive substance such as a bitter or umami substance to a molecular film can be measured, so that the response to a taste component corresponding to an adsorptive substance can be separated from the response to a taste component corresponding to a non-adsorptive substance such as a sour or salty substance to the molecular film, thereby increasing the taste information quantity.

The application examples of the present invention will be described below.

(1) Measurement of Bitterness of Beer

An application example of the present invention to the qualitative analysis of bitterness of beer will be described below.

Bitterness is most important in the tastes of beer and is regarded to be derived from iso-$\alpha$ acid.

For this reason, a method of measuring the quantity of this iso-$\alpha$ acid is internationally standardized in the beer industry (bitterness value).

It takes normally several hours to complete this analysis. According to the measurement method of the present invention, however, it takes only several minutes to complete this analysis.

In lipid membranes like the ones Nos. 4 and 5 which have positive charges in an aqueous solution, the positive charges are strongly bonded to bitterness components, i.e., iso-$\alpha$ acid as the negative charges. The adsorption quantity of other taste substances is small. According to the measurement method of the present invention, therefore, a signal representing only iso-$\alpha$ acid can be detected.

The reason for this is not clarified yet. However, when a lipid membrane having negative charges is adsorbed in a lipid membrane having positive charges, the sensitivity and selectivity of iso-$\alpha$ acid tend to increase.

The actual measurement results of 19 Japanese beer brands are shown in FIG. 27A.

The reference solution in this measurement is a solution mixture containing 5% of ethanol, 30 mM of KCl, and 0.3 mM of tartaric acid. The sensor has film No. 6 in Table 2.

The measurement sequence follows the same procedures as in FIG. 1.

$\Delta Vki$ (mV) in FIG. 1 is plotted along the ordinate of FIG. 27A, and the bitterness value associated with the concentration of the iso-$\alpha$ acid and used as a value representing bitterness in the beer industry is plotted along the abscissa of FIG. 27A.

Referring to FIG. 27A, the average value of the four measurement results per sample is indicated by an open circle, and the magnitude of the measurement error (standard deviation) is indicated by a bar.

According to this representation, a brand having a larger bitterness value has a sensor output value toward the negative direction. This indicates a larger adsorption quantity.

The correlation coefficient between the bitterness value and the sensor output is 0.9, and the bitterness value can be estimated from the sensor output.

To improve the precision for estimating this bitterness value, other sensor outputs are used, as a matter of course. When a multiple regression analysis is performed using all the sensor outputs (including relative values) shown in Table 2, the multiple correlation coefficient can be improved up to 0.999.

(2) Measurement of Green Tea

An application example of the present invention to the quantitative measurement of astringency of green tea will be described below.

Astringency is most important in teas including green tea and is regarded to be derived from mainly tannic acid.

A liquid chromatograph is normally used in measurement of tannic acid. Setup and measurement require several hours.

However, when the measurement method of the present invention is used, the measurement of tannic acid can be completed within several minutes.

In lipid membranes like the ones Nos. 4 and 5 which have positive charges in an aqueous solution, the positive charges are strongly bonded to astringent components, i.e., tannic acid as the negative charges. The adsorption quantity of other taste substances is small. According to the measurement method of the present invention, therefore, a signal representing only tannic acid can be detected.

The reason for this is not clarified yet. However, when a lipid membrane having negative charges is adsorbed in a lipid membrane having positive charges, the sensitivity and selectivity of tannic acid tend to increase.

The actual measurement results of 22 green tea brands are shown in FIG. 27B.

The reference solution in this measurement is a solution mixture containing 30 mM of KCl, and 0.3 mM of tartaric acid. The sensor has film No. 6 in Table 2.

The measurement sequence follows the same procedures as in FIG. 1.

$\Delta Vki$ (mV) in FIG. 1 is plotted along the ordinate of FIG. 27B, and the tannin analysis value associated with the concentration of the tannic acid is plotted along he abscissa of FIG. 27B. The average value of the four measurement results per sample is indicated by an open circle, and the magnitude of the measurement error (standard deviation) is indicated by a bar.

According to this representation, a brand having a larger tannin analysis value has a sensor output value toward the negative direction. This indicates a larger adsorption quantity.

The correlation coefficient between the tannin analysis value and the sensor output is 0.91, and the tannin analysis value can be estimated from the sensor output.

To improve the precision for estimating this tannin analysis value, other sensor outputs are used, as a matter of course. When a multiple regression analysis is performed using all the sensor outputs (including relative values) shown in Table 2, the multiple correlation coefficient can be improved up to 0.999.

(3) Other Measurements

The applicability of the present invention to quantitative measurements of umami and bitterness will be described below.

When the measurement method of the present invention is practiced using a mixed membrane consisting of a lipid having positive charges and a lipid having negative charges, this mixed membrane has sensitivities and selectivities to an umami substance and bitter and astringent substances as negative charges.

A lipid membrane having positive charges has a sensitivity and selectivity to bitter and astringent substances having negative charges.

By combining the sensor outputs from these two types of lipid membranes, umami can be quantitatively measured.

When the measurement method of the present invention is practiced using a lipid membrane having positive charges, the lipid membrane has sensitivities and selectivities to stringent and bitter substances having negative charges.

When the measurement method of the present invention is practiced using a lipid membrane having negative charges, the lipid membrane has a sensitivity and selectivity to a bitter substance having positive charges.

By combining the sensor outputs from these two types of lipid membranes, total quantitative analyzing of astringency and bitterness can be provided regardless of the types of charges.

As described above, according to the present invention, desired reference solutions are prepared. A sensor potential V01 in the first reference solution is measured. The sensor is dipped in a target measurement solution containing an ionic adsorption substance for a predetermined period of time, and then a sensor potential V02 in the second reference solution is measured. The difference between the sensor potentials V01 and V02 is obtained.

This difference is obtained to cancel drift components. The reason for this will be described in detail below.

As described above, when a taste substance is adsorbed in a taste sensor, the charge density on the surface of the taste sensor changes, and the characteristics of the taste sensor change.

No membrane characteristics change in a taste substance having no adsorption properties, such as salt.

For example, quinine (bitterness) is strongly adsorbed in a dioctyl phosphate film in Table 2, and the membrane originally having negative charges becomes a membrane having positive (quinine has positive charges in water) charges, thereby changing its characteristics.

According to the present invention, a change in characteristics of the lipid membrane is detected to detect only an adsorptive taste substance among taste substances.

A solution for detecting the change in characteristics of the lipid membrane is a reference solution.

FIG. 28 shows a conceptual view.

The logarithm (logC) of a concentration C of the reference solution is plotted along the abscissa of FIG. 28, and the corresponding values of the taste sensor are plotted along the ordinate of FIG. 28.

The corresponding characteristics in the absence of adsorption of taste substances in a taste sensor are represented by thick lines. The response characteristics of the taste sensor upon dipping the taste sensor in a test solution, i.e., in a state wherein taste substances are adsorbed in the taste sensor are represented by thin lines.

Changes in characteristics caused by adsorption are detected. For this purpose, the response values of the reference solution at a given concentration C0 are compared to determine specific adsorption quantities.

A difference $\Delta Vk$ between the response value before adsorption and the response value after adsorption is obtained (the first and second reference solutions are identical to each other). The zero difference $\Delta Vk$ indicates that no adsorption substance is present in the test solution. The difference $\Delta Vk$ having a larger absolute value indicates a higher adsorption substance concentration in the test solution.

If the sensor response value is free from drifts, the difference need not be calculated in every measurement.

However, many taste sensor have drifts, and the difference must be calculated.

Note that the first reference solution may be different from the second reference solution.

Information correlated with the adsorption quantity need only be obtained. For this purpose, the second reference solution used after the taste sensor is dipped in the test solution may be the same type of solution as in measurement in the test solution to be compared.

As described above, when the first and second reference solutions are identical to each other, the zero difference $\Delta Vk$ corresponds to zero adsorption.

The first reference solution is used to reduce sensor drifts. The taste sensor can perform a stabler measurement when the concentration of the first reference solution is higher.

The second reference solution is used to detect any change in characteristics of the taste sensor upon adsorption. As can be apparent from FIG. 28, the difference in the degree of adsorption appears more easily at lower concentrations of the second reference solution.

More specifically, a lipid membrane having negative charges in an aqueous solution has a higher membrane potential in the negative direction and the adsorption difference described above tends to appear more easily as the pH is higher and the electrical conductivity is lower.

A lipid membrane having positive charges in an aqueous solution has a higher membrane potential in the positive direction and the adsorption difference described above tends to appear more easily as the electrical conductivity is lower.

Judging from the above description, to obtain a satisfactory effect, the pH of the second reference solution must be higher than that of the first reference solution by 0.3 or more, and the electrical conductivity of the second solution must be ½ or less of that of the first reference solution.

Drifts can be reduced although the difference between the first and second reference solutions is not directly calculated. A calibration test solution is prepared. The response value of a test sensor in the second reference solution in calibration test solution measurement is subtracted from the response value of the test sensor in the second reference solution in each test solution measurement, thereby reducing drifts.

Since the change in characteristics of the taste sensor which is caused by an adsorption substance must be detected, a change in sensitivity for salt (or an acid) before dipping the taste sensor in the test solution and after dipping the test sensor in the test solution may be measured.

That is, this is because the resultant change in sensitivity includes concentration information of the adsorption substance in the test solution.

In this case, as the change in sensitivity is to be measured, the second reference solution must be constituted by at least two reference solutions having different concentrations.

Sensor films cleaned by a variety of cleaning solutions employed in the present invention will be briefly described.

1. Since organic solvents diluted with water are effective to almost all of the sensor films, of adsorptive substances, a highly hydrophobic adsorptive substance which is strongly adsorbed in the hydrophobic portion of the film is cleaned using the hydrophobic properties of an organic solvent.

2. Since an acid is particularly effective to a lipid membrane, such as a phosphorus lipid having negative charges, of the adsorptive substances, an adsorptive substance which is positively charged and chemically reacts with the negative functional group of the lipid to produce a salt is used utilizing the hydrogen ion exchange action of the acid.

Thereafter, the hydrogen ions are eliminated (dissociation of the functional group of the lipid) by co-washing in the reference solution or stabilization in the reference solution, thereby restoring the original state.

At this time, after acid cleaning, excessive hydrogen ions can be eliminated by simple rinsing in a neutral or weak alkali solution, thereby increasing the measurement speed.

This acid action can be obtained even by a salt such as sodium chloride or potassium chloride. However, the substitution action of sodium and potassium ions is about 1/100 that of the hydrogen ions. This salt action cannot be expected to yield a great effect as compared with the above acid action.

3. Since salt is particular y effective to a lipid having a group (e.g., an ammonium group) charged with positive charges, of the adsorptive substances, an adsorptive substance which is positively charged and chemically reacts with the positive functional group of the lipid to produce a salt is used utilizing the substitution function of negative ions such as chlorine ions of salt.

Thereafter, the chlorine ions are eliminated (dissociation of the functional group of the lipid) by co-washing in the reference solution or stabilization in the reference solution, thereby restoring the original state.

At this time, after salt cleaning, excessive chlorine ions can be eliminated by simple rinsing in pure water, thereby increasing the measurement speed.

This salt action may be replaced with an acid such as hydrochloric acid. However, since the substitution effect cannot be expected until the concentration of chlorine ions as negative ions is set high, an acid must also have a high concentration, resulting in a difficulty in handling.

4. An alkali is particularly effective for a lipid having an ammonium group.

A hydrogen ion is arranged and combined to the ammonium group, and a negatively charged adsorptive substance is chemically reacted to produce a salt at this hydrogen ion portion.

When an alkali is added, the ammonium group is unbonded from the hydrogen ion, and the adsorption substance is also eliminated together with the hydrogen ion.

By using this action, cleaning is performed.

The hydrogen ion is arranged and combined to the ammonium group by co-washing in the reference solution and stabilization in the reference solution, thereby restoring the original state.

At this time, after alkali cleaning, excessive hydrogen ions can be eliminated by simple rinsing in the acid solution, thereby increasing the measurement speed.

5. Some films require different cleaning solutions depending on the types of substances adsorbed thereto.

For example, in case of "salt" such as table salt or natural salt has only inorganic ions, cleaning using only an acid is enough to eliminate calcium and magnesium serving as bitter components.

A predetermined degree of cleaning will be described below.

After a taste sensor is dipped in a target measurement solution, cleaning is performed in a certain degree prior to the measurement in the second reference solution.

This cleaning is called post-cleaning.

The difference $\Delta Vk$ changes depending on the strength of post-cleaning and the types of cleaning. This change can serve as new taste information.

In particular, when the degree of post-cleaning is changed, the human tongue can sense an aftertaste. When the type of post-cleaning is changed, the selectivity to an adsorption substance can be improved.

The phosphorus lipid membrane shown in FIG. 8A adsorbs bittern (a taste similar to bitterness of Ca, Mg, or the like). As compared with quinine exhibiting bitterness 6 in FIG. 8B, the above lipid membrane has a weaker adsorption power.

Upon completion of measurement of a target measurement solution, when a sensor is subjected to co-washing as post-cleaning in a reference solution about 10 times, the difference $\Delta Vk$ (the first and second reference solutions are identical to each other) of bittern comes close to zero, but the difference $\Delta Vk$ of quinine still has a large value.

Quinine exhibits strong and pure bitterness, while bittern exhibits weak and vague bitterness. Therefore, quinine can be distinguished from bittern in accordance with the degree of cleaning upon dipping the sensor in the target measurement solution.

More specifically, when the number of times of co-washing as post-washing is increased, and the difference $\Delta Vk$ value decreases, the bitterness is light and without any aftertaste. However, when the difference $\Delta Vk$ value does not decrease, the bitterness is strong and has an aftertaste.

It is very important to distinguish a weak aftertaste from a strong aftertaste in bitterness. This distinction can be made by performing post-cleaning.

An oleyl amine membrane adsorbs milk (this membrane also adsorbs salt, but when co-washing as post-cleaning is performed about 10 times, the difference $\Delta Vk$ value becomes zero, but the difference $\Delta Vk$ value of milk remains large).

The oleyl amine membrane also adsorbs bitterness (iso-$\alpha$ acid) of beer and astringency (tannic acid) of tea from FIGS. 27A and 27B.

That is, the difference $\Delta Vk$ of oleyl amine represents three tastes, i.e., milk, bitterness, and astringency.

The oleyl amine membrane has a cleaning effect in an aqueous solution containing ethanol except for an alkali for milk components. The oleyl amine has a cleaning effect in an aqueous alkali solution containing ethanol for bitterness and astringency.

By utilizing the above actions, when an aqueous alkali solution is used in post-cleaning, the oleyl amine can respond to only milk, or bitterness and astringency.

When an aqueous solution containing ethanol except for an alkali is used in post-cleaning, the milk components are cleaned, and bitterness and astringency are left. When an aqueous alkali solution containing ethanol is used in post-cleaning, bitter and astringent components are cleaned, and only the milk components are left.

In each of the first to seventh embodiments, the membrane potential is measured as a response of a taste sensor to a taste substance. However, the measurement is not limited to the membrane potential, but the membrane resistance (ionic permeability) can be measured.

More specifically, the electrical characteristics of a lipid membrane change depending on different taste substances. The membrane potentials and the membrane resistances (ionic permeability) are influenced differently for the above-mentioned five basic tastes, as described in detail on pp. 71 and 72 in "Taste Sensor More Sensitive than Man", Nikkei Science, October issue, 1991, pp. 68–76.

As a measurement method of the membrane resistance (ionic permeability: impedance), the Lissajous method using a galvanostat, an AC bridge method using a potentiostat, and a phase discrimination method are known well in the field of electrochemistry, and a description thereof will be omitted.

According to the present invention, therefore, components including the membrane potential and the membrane resistance (ionic permeability) are called the responses of the taste sensor.

According to the present invention, taste information can also be obtained using transient response characteristics.

More specifically, in each of the first to seventh embodiments described above, measurement is performed once after a predetermined period of time as a taste sensor response to a taste substance. The present invention is not limited to this. Measurement can be performed several times at a predetermined time interval, and taste information can also be obtained from a change in measurement values during the total measurement time.

For example, a transient response upon dipping the taste sensor in the second sensor after the taste sensor is dipped in the test solution is deemed to serve as taste information.

As described above, for a highly adsorptive substance such as quinine, the difference $\Delta Vk$ value (the first and second reference solutions are identical to each other) in terms of the taste sensor response, i.e., the membrane potential and the membrane resistance (ionic permeability) is almost constant and stable.

An adsorptive substance having poor adsorption properties, such as bittern tends to be eliminated while the taste sensor is dipped in the second reference solution. A time change in taste sensor response, i.e., the film potential and the membrane resistance (ionic permeability), comes to close to zero, provided that the first and second reference solutions are identical to each other.

As has been described in detail, according to the present invention, there can be provided a taste measurement method capable of increasing the taste information quantity.

INDUSTRIAL APPLICABILITY

In taste measurement, the output signal from a sensor is analyzed into, e.g. principal components analysis. Result of principal components analysis are compared with samples learned in advance, and are classified. These principal components are two-dimensionally displayed on a display to form a taste map. Therefore, the distribution state of the samples can be visually grasped by this map, thereby facilitating classification of the samples and comparison with functional data.

Alternatively, multiple regression analysis may be performed in place of the principal component analysis.

As disclosed in Jpn. Pat. Appln. KOKAI Publication No. 5-99896, the sensitivity of each sensor to each original taste is obtained, and the sensor response can be modeled (more specifically, simultaneous equations having the strength of each original taste as an unknown are written based on the sensor outputs and the sensitivities). The simultaneous equations are solved to obtain numerical values quantitatively representing the strengths of the respective original tastes. The numerical values are then corrected to values representing the strengths of the respective original tastes matching the human tastes. Therefore, the tastes can be quantitatively expressed.

Therefore, the present invention strongly supports the panelists, e.g., in quality control of beverage and food products and the development of a new product. The analysis and discrimination precision and the development efficiency can be greatly improved.

I claim:

1. A taste measurement method for obtaining taste information of a target measurement solution using a taste sensor with a molecular film for an amphiphatic or bitter substance, comprising the steps of:

dipping said taste sensor in the target measurement solution for a predetermined period of time;

removing, from the target measurement solution, said taste sensor which has been dipped in the target measurement solution for the predetermined period of time, without obtaining a sensor response; and subsequently dipping said taste sensor, which was removed from the target measurement solution, in a reference solution to obtain a sensor response, wherein the obtained sensor response is defined as the taste information of the target measurement solution.

2. A taste measurement method for obtaining taste information of a target measurement solution using a taste sensor with a molecular film for an amphiphatic or bitter substance, comprising the steps of:

dipping said taste sensor in a first reference solution to obtain a first sensor response;

after the first sensor response is obtained, removing said taste sensor from the first reference solution;

dipping said taste sensor removed from the first reference solution in the target measurement solution for a predetermined period of time;

removing, from the target measurement solution, said taste sensor which has been dipped in the target measurement solution for the predetermined period of time, without obtaining a sensor response;

subsequently dipping said taste sensor, which was removed from the target measurement solution, in a second reference solution to obtain a second sensor response; and obtaining a difference between the first and second sensor responses, wherein the obtained difference between the first and second sensor responses is defined as the taste information of the target measurement solution.

3. A taste measurement method according to claim 1, including the step of cleaning said taste sensor to a desired degree after the step of removing said taste sensor from the target measurement solution.

4. A taste measurement method according to claim 1, including the step of cleaning a desired adsorption substance in said taste sensor after the step of removing said taste sensor from the target measurement solution.

5. A taste measurement method according to claim 2, including the steps of cleaning said taste sensor and measuring a next target measurement solution after the step of obtaining the difference between the first and second sensor responses.

6. A taste measurement method according to claim 2, wherein the second reference solution has at least one of a pH higher than that of the first reference solution by 0.3 or more and an electrical conductivity ½ or less of that of the first reference solution.

7. A taste measurement method according to claim 1, wherein the sensor responses are transient responses.

8. A taste measurement method according to claim 1, wherein the sensor responses are membrane potentials.

9. A taste measurement method according to claim 1, wherein the sensor responses are membrane resistances.

10. A taste measurement method according to claim 2, including the step of cleaning said taste sensor to a desired degree after the step of removing said taste sensor from the target measurement solution.

11. A taste measurement method according to claim 2, including the step of cleaning a desired adsorption substance in said taste sensor after the step of removing said taste sensor from the target measurement solution.

12. A taste measurement method according to claim 2, wherein the sensor responses are transient responses.

13. A taste measurement method according to claim 2, wherein the sensor responses are membrane potentials.

14. A taste measurement method according to claim 2, wherein the sensor responses are membrane resistances.

* * * * *